(12) United States Patent
Jackson

(10) Patent No.: US 9,788,868 B2
(45) Date of Patent: Oct. 17, 2017

(54) DYNAMIC SPINAL STABILIZATION ASSEMBLIES, TOOL SET AND METHOD

(71) Applicant: Roger P Jackson, Prairie Village, KS (US)

(72) Inventor: Roger P Jackson, Prairie Village, KS (US)

( * ) Notice: Subject to any disclaimer, the term of this patent is extended or adjusted under 35 U.S.C. 154(b) by 0 days.

(21) Appl. No.: 14/938,485

(22) Filed: Nov. 11, 2015

(65) Prior Publication Data

US 2016/0074077 A1   Mar. 17, 2016

Related U.S. Application Data

(63) Continuation of application No. 12/927,673, filed on Nov. 19, 2010, now Pat. No. 9,216,039, which is a (Continued)

(51) Int. Cl.
*A61B 17/56* (2006.01)
*A61B 17/58* (2006.01)
(Continued)

(52) U.S. Cl.
CPC ...... *A61B 17/7082* (2013.01); *A61B 17/7002* (2013.01); *A61B 17/7028* (2013.01);
(Continued)

(58) Field of Classification Search
CPC ........ A61B 17/7032; A61B 2017/0256; A01B 12/006
See application file for complete search history.

(56) References Cited

U.S. PATENT DOCUMENTS

| 854,956 A | 5/1907 | Martin |
| 2,243,717 A | 5/1941 | Godoy et al. |

(Continued)

FOREIGN PATENT DOCUMENTS

| DE | 20207850 | 10/2002 |
| WO | WO 95/13755 | 5/1995 |

OTHER PUBLICATIONS

European Seach Report, EP14189707.4, dated Feb. 25, 2015.

*Primary Examiner* — David Isabella
*Assistant Examiner* — Christine Nelson
(74) *Attorney, Agent, or Firm* — Polsinelli PC

(57) ABSTRACT

A hinged bone screw and tool set is used for implanting such bone screws in a human spine, followed by the implantation of a longitudinal connecting member into the bone screws. The hinged bone screw includes a shank with an upper portion and a receiver with integral arms forming a U-shaped channel. A lower curved seat partially defining the U-shaped channel cooperates with an upper portion of the bone screw shank for hinged movement of the shank with respect to the receiver. The tool set includes an insertion tool, a bone screw driver, a reduction tool and a closure starter. The insertion tool includes a bone screw attachment structure and a laterally opening channel. The insertion tool further includes a threaded portion for cooperation with the reduction tool to provide synchronized placement of a closure structure in the bone screw receiver while reducing and capturing a longitudinal connecting member within the receiver. Further alternative bone screws are hinged, polyaxial or fixed and include lordosing or kyphosing lateral surfaces.

13 Claims, 19 Drawing Sheets

Related U.S. Application Data continuation of application No. 11/328,481, filed on Jan. 9, 2006, now Pat. No. 7,862,587, which is a continuation-in-part of application No. 11/272,508, filed on Nov. 10, 2005, now Pat. No. 9,050,148, which is a continuation-in-part of application No. 10/996,289, filed on Nov. 23, 2004, now Pat. No. 8,152,810, and a continuation-in-part of application No. 10/789,149, filed on Feb. 27, 2004, now Pat. No. 7,160,300.

(60) Provisional application No. 60/722,300, filed on Sep. 30, 2005, provisional application No. 60/725,445, filed on Oct. 11, 2005, provisional application No. 60/728,912, filed on Oct. 21, 2005, provisional application No. 60/736,112, filed on Nov. 10, 2005, provisional application No. 60/630,536, filed on Nov. 23, 2004.

(51) Int. Cl.
*A61F 2/30* (2006.01)
*A61B 17/70* (2006.01)
*A61B 17/86* (2006.01)
*A61B 17/88* (2006.01)

(52) U.S. Cl.
CPC ...... *A61B 17/7032* (2013.01); *A61B 17/7037* (2013.01); *A61B 17/7038* (2013.01); *A61B 17/7076* (2013.01); *A61B 17/7085* (2013.01); *A61B 17/7089* (2013.01); *A61B 17/7091* (2013.01); *A61B 17/861* (2013.01); *A61B 17/7004* (2013.01); *A61B 17/7011* (2013.01); *A61B 17/7031* (2013.01); *A61B 17/8875* (2013.01)

(56) References Cited

U.S. PATENT DOCUMENTS

| | | |
|---|---|---|
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 4,269,178 A | 5/1981 | Keene |
| 5,020,519 A | 6/1991 | Hayes |
| D346,217 S | 4/1994 | Sparker |
| 5,443,467 A | 8/1995 | Biedermann et al. |
| 5,961,517 A | 10/1999 | Biedermann et al. |
| 6,077,262 A | 6/2000 | Schlapfer et al. |
| 6,139,549 A | 10/2000 | Keller |
| 6,214,012 B1 | 4/2001 | Karpman et al. |
| 6,280,442 B1 | 8/2001 | Barker et al. |
| 6,440,133 B1 | 8/2002 | Beale et al. |
| 6,530,929 B1 | 3/2003 | Justis et al. |
| 6,648,888 B1 | 11/2003 | Shluzas |
| 6,730,089 B2 | 5/2004 | Jackson |
| 6,755,829 B1 | 6/2004 | Bono et al. |
| 6,837,889 B2 | 1/2005 | Shluzas |
| 6,911,030 B1 | 6/2005 | Vanacker et al. |
| 6,932,822 B2 | 8/2005 | Oribe et al. |
| 7,066,937 B2 | 6/2006 | Shluzas |
| 7,090,679 B2 | 8/2006 | Saint-Martin et al. |
| 7,160,300 B2 | 1/2007 | Jackson |
| 7,250,052 B2 * | 7/2007 | Landry ............ A61B 17/1604 606/86 A |
| 7,377,923 B2 | 5/2008 | Purcell et al. |
| 7,527,638 B2 | 5/2009 | Anderson et al. |
| 7,547,318 B2 | 6/2009 | Birkmeyer et al. |
| 7,666,188 B2 | 2/2010 | Anderson et al. |
| 7,708,763 B2 | 5/2010 | Selover et al. |
| 7,722,651 B2 | 5/2010 | Kwak et al. |
| 7,862,587 B2 | 1/2011 | Jackson |
| 7,951,172 B2 | 5/2011 | Chao et al. |
| 7,985,242 B2 | 7/2011 | Forton et al. |
| 8,034,084 B2 | 10/2011 | Landry et al. |
| 8,066,739 B2 | 11/2011 | Jackson |
| 8,075,592 B2 | 12/2011 | Landry et al. |
| 8,100,915 B2 | 1/2012 | Jackson |
| 8,162,948 B2 | 4/2012 | Jackson |
| 8,377,067 B2 | 2/2013 | Jackson |
| 9,050,148 B2 | 6/2015 | Jackson |
| 9,101,415 B2 | 8/2015 | Jackson |
| 9,173,682 B2 | 11/2015 | Jackson |
| 9,216,039 B2 | 12/2015 | Jackson |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 9,532,815 B2 | 1/2017 | Jackson |
| 2002/0026193 A1 | 2/2002 | Barker et al. |
| 2002/0133154 A1 | 9/2002 | Saint Martin |
| 2002/0143341 A1 | 10/2002 | Biedermann et al. |
| 2003/0023240 A1 | 1/2003 | Amrein et al. |
| 2003/0100904 A1 | 5/2003 | Biedermann |
| 2004/0143265 A1 | 7/2004 | Landry et al. |
| 2004/0167525 A1 | 8/2004 | Jackson |
| 2004/0172022 A1 | 9/2004 | Landry et al. |
| 2005/0131408 A1 | 6/2005 | Sicvol et al. |
| 2005/0149036 A1 | 7/2005 | Varieur et al. |
| 2005/0192573 A1 | 9/2005 | Abdelgany et al. |
| 2006/0079909 A1 | 4/2006 | Runco |
| 2012/0071886 A1 | 3/2012 | Jackson |
| 2013/0304130 A1 | 11/2013 | Jackson |
| 2014/0222090 A1 | 8/2014 | Jackson |
| 2015/0080974 A1 | 3/2015 | Jackson |
| 2015/0142060 A1 | 5/2015 | Jackson |
| 2015/0182258 A1 | 7/2015 | Jackson |
| 2015/0265322 A1 | 9/2015 | Jackson |
| 2015/0272631 A1 | 10/2015 | Jackson |
| 2016/0015433 A1 | 1/2016 | Jackson |
| 2017/0135731 A1 | 5/2017 | Jackson |

\* cited by examiner

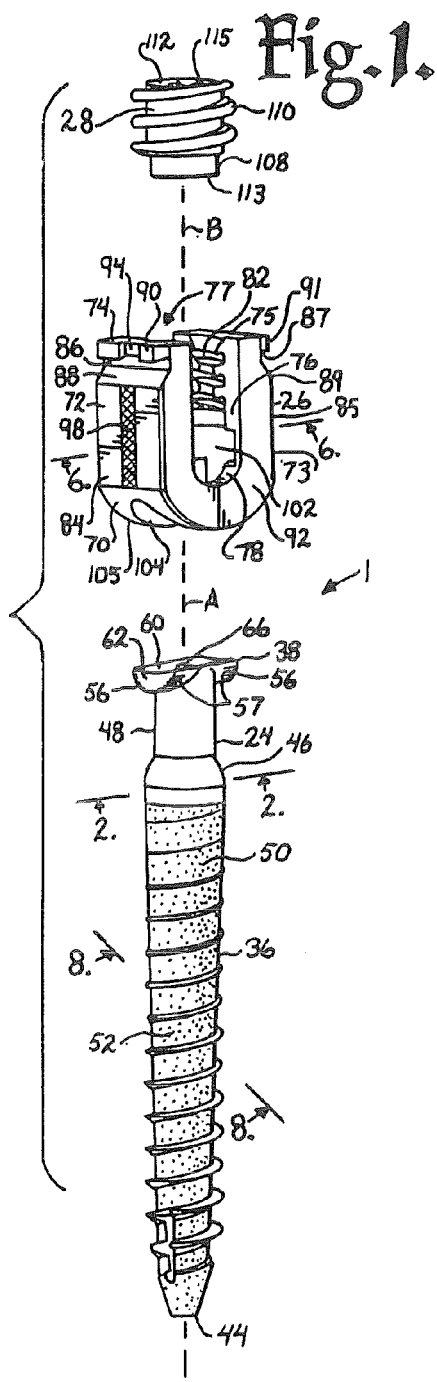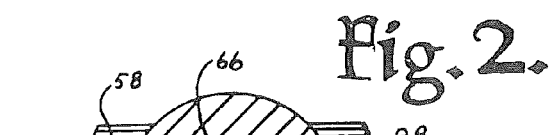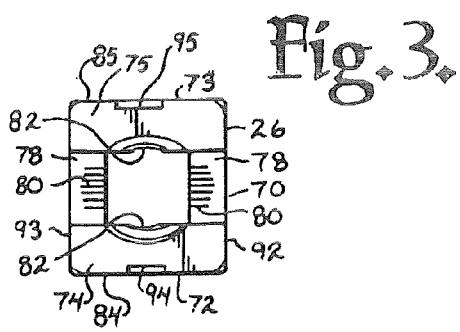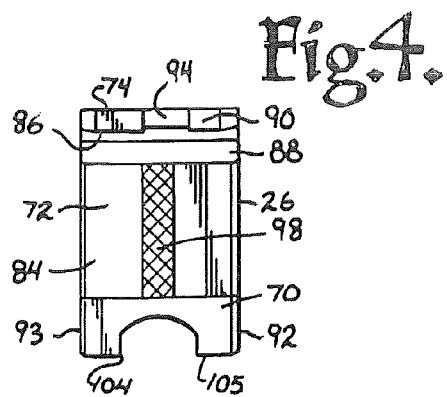

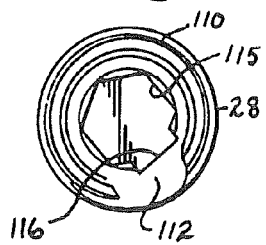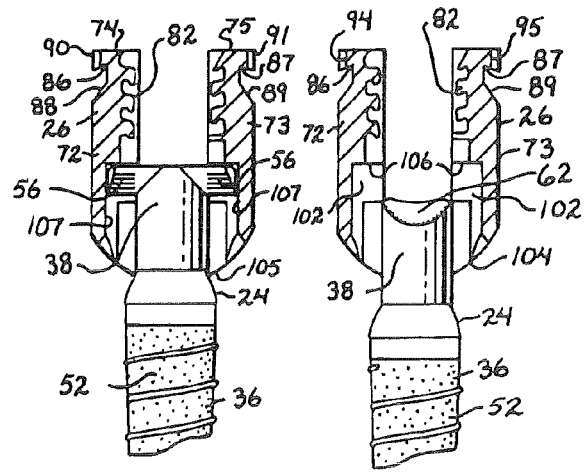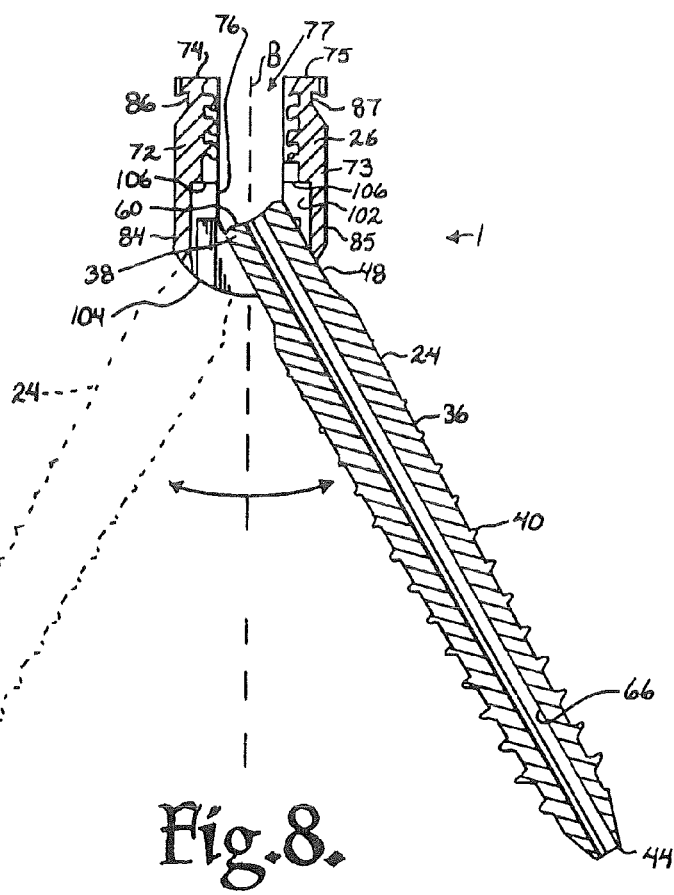

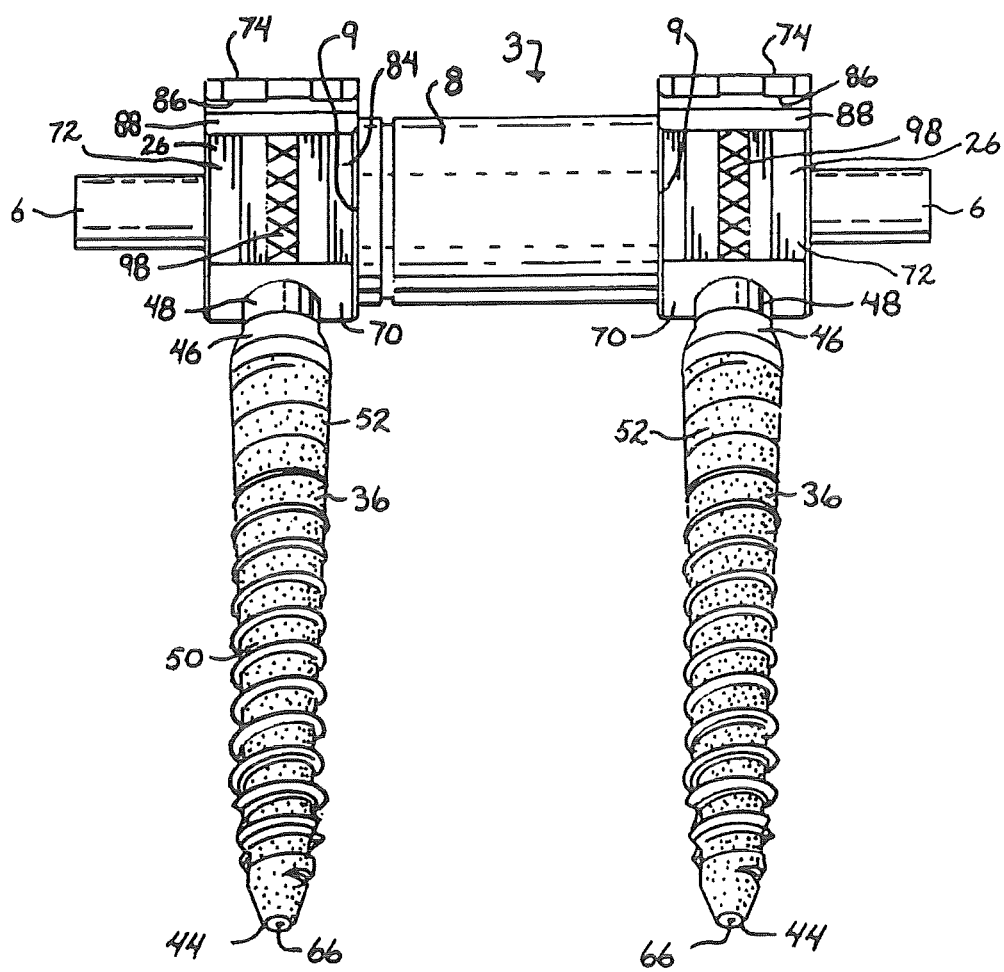

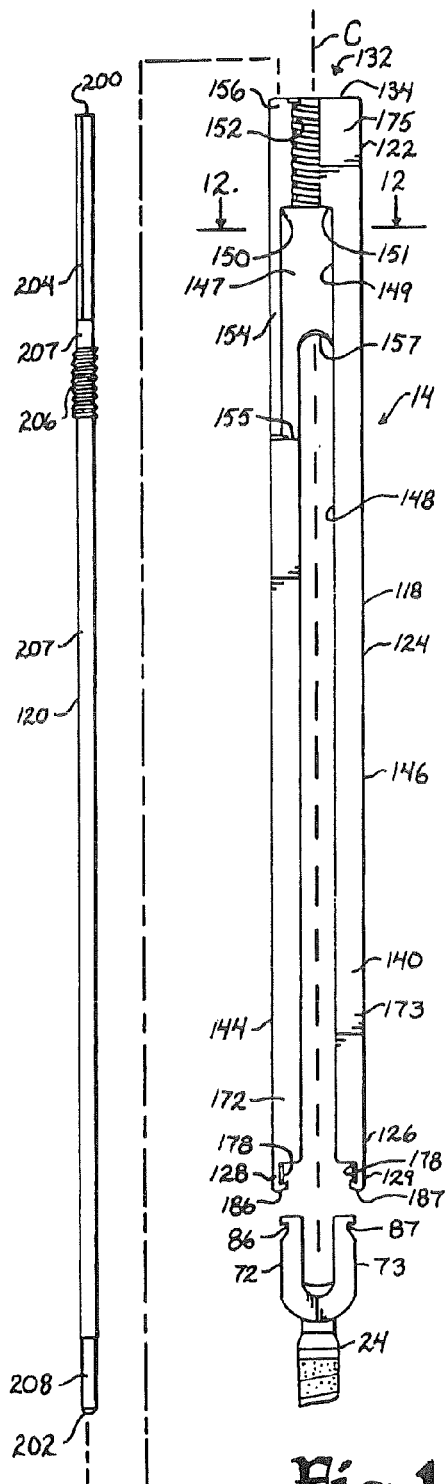
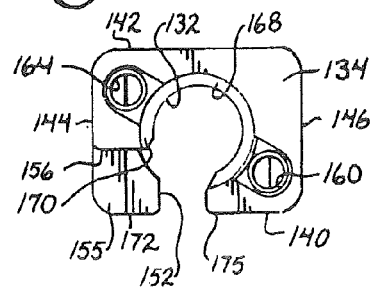
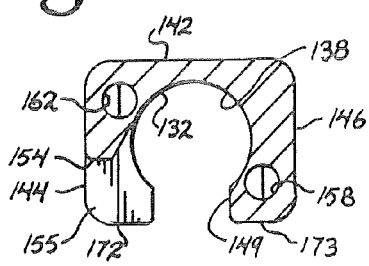
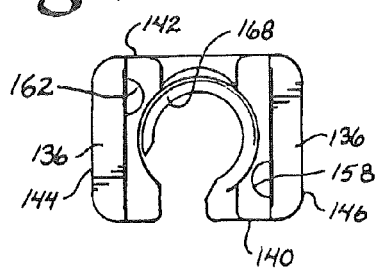

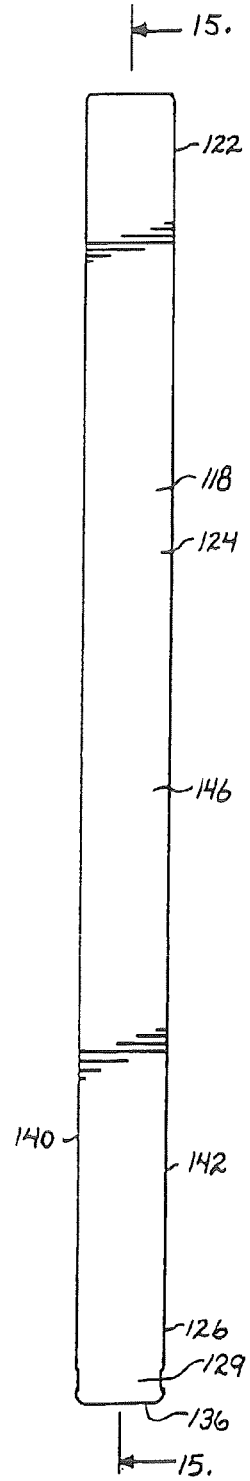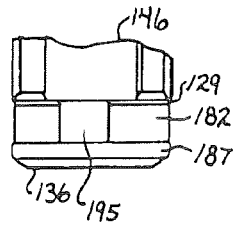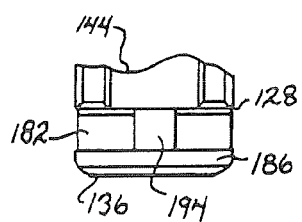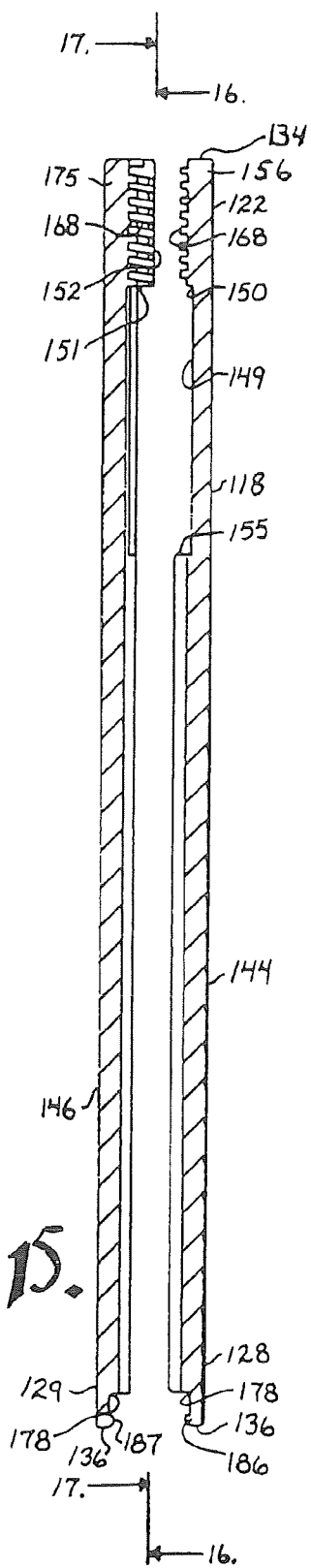

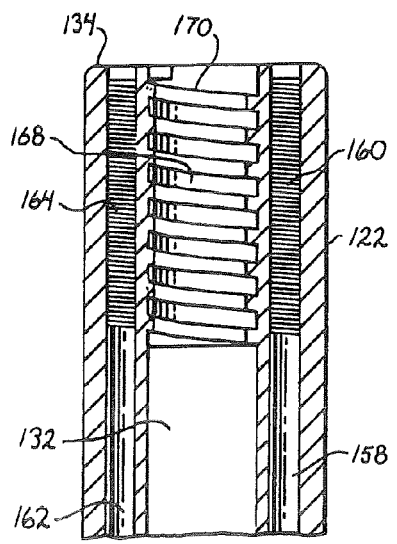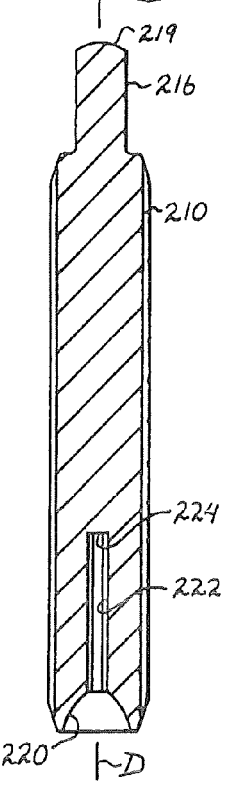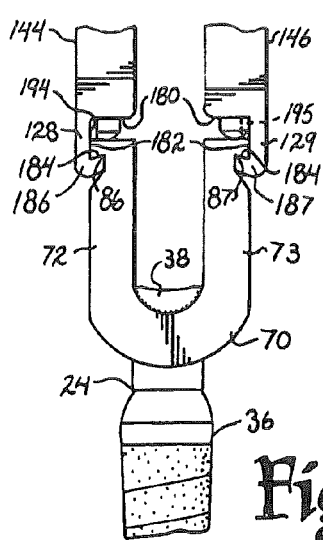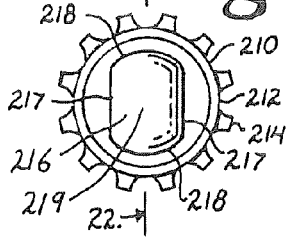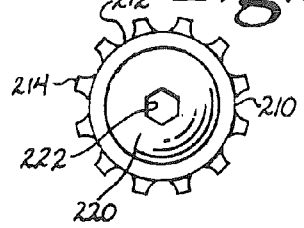

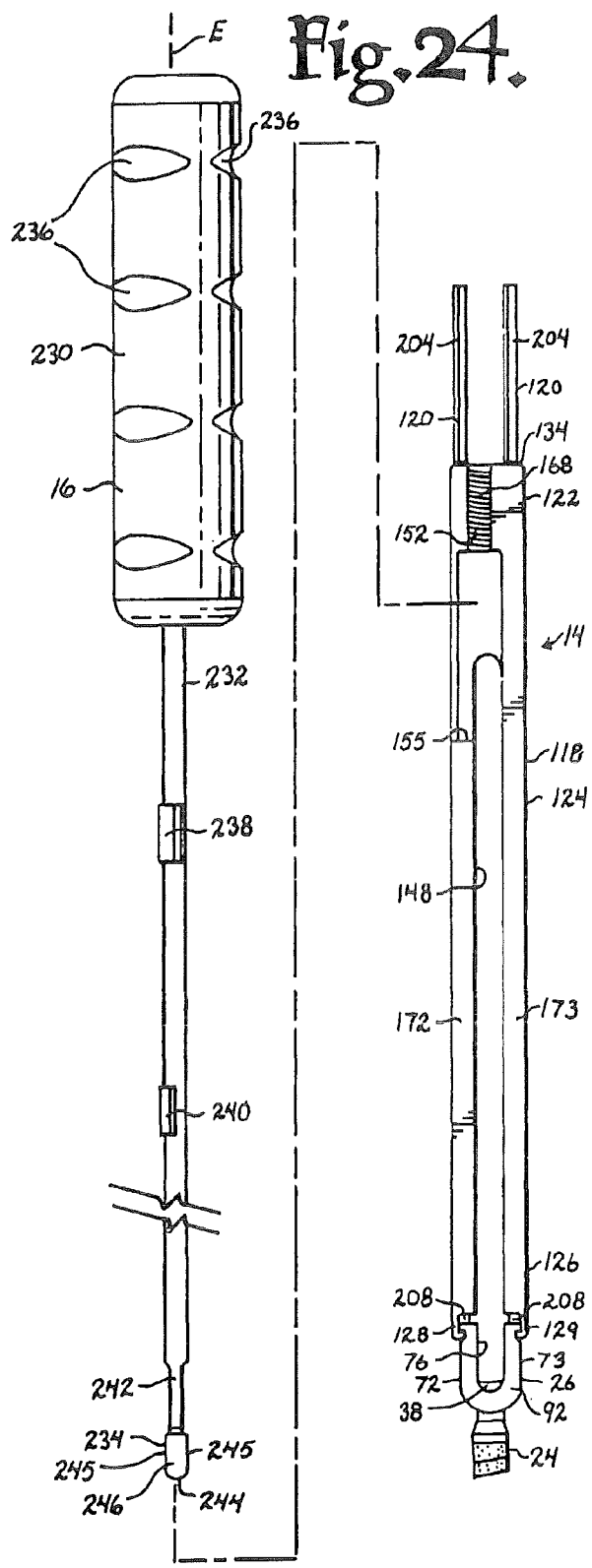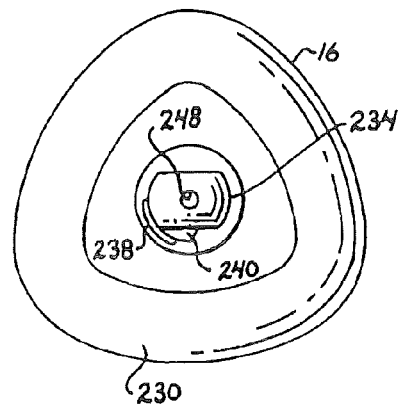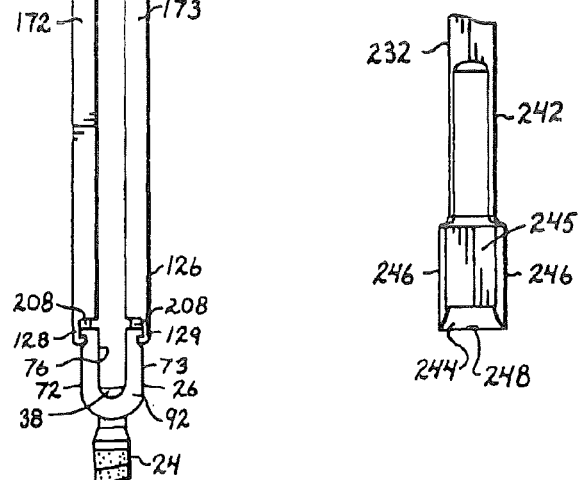

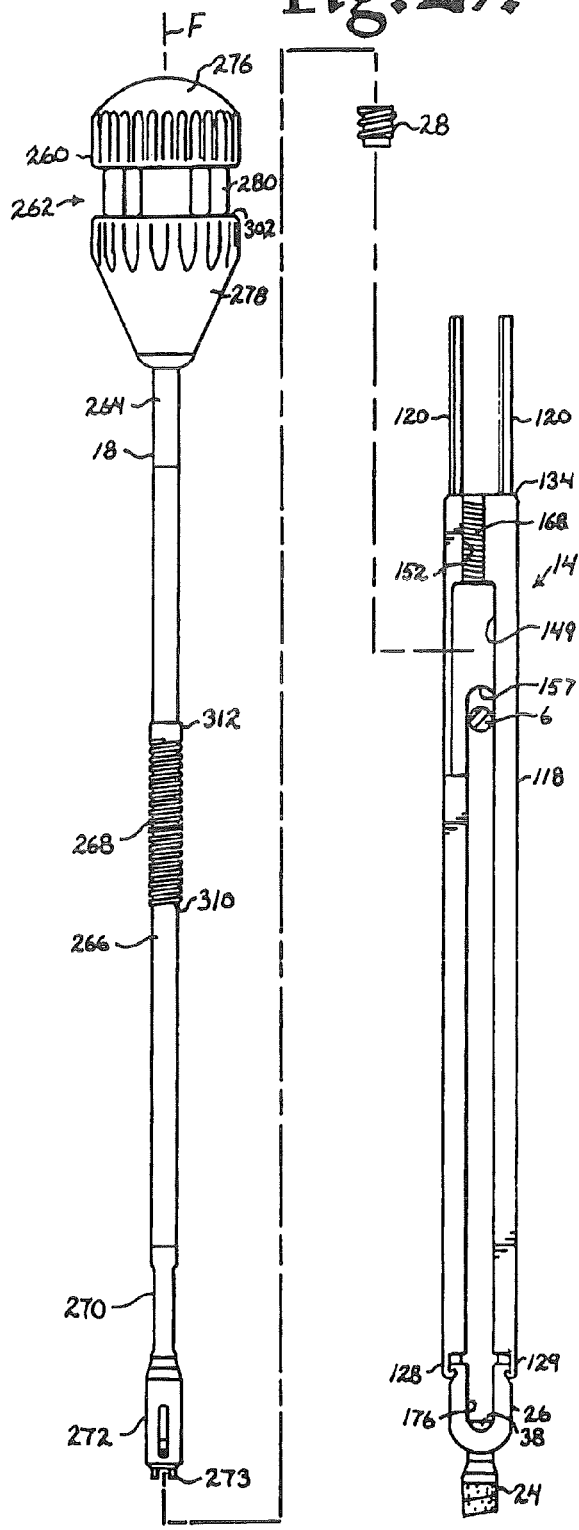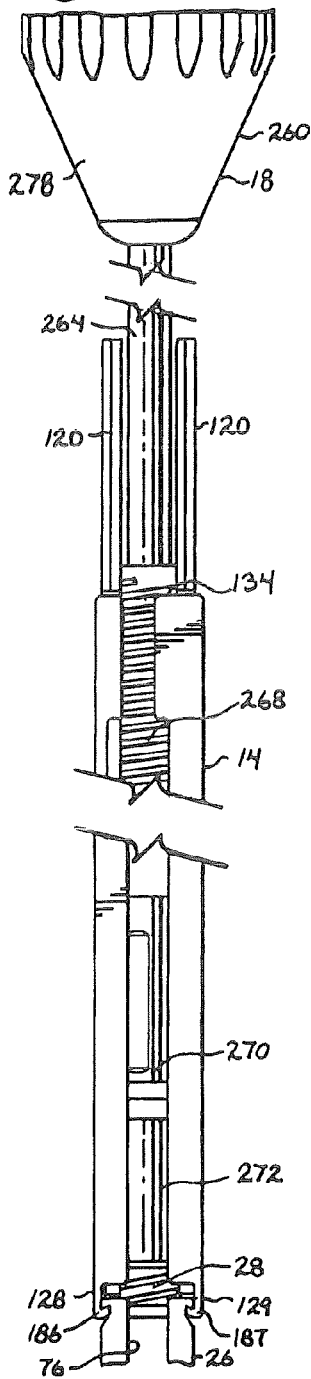

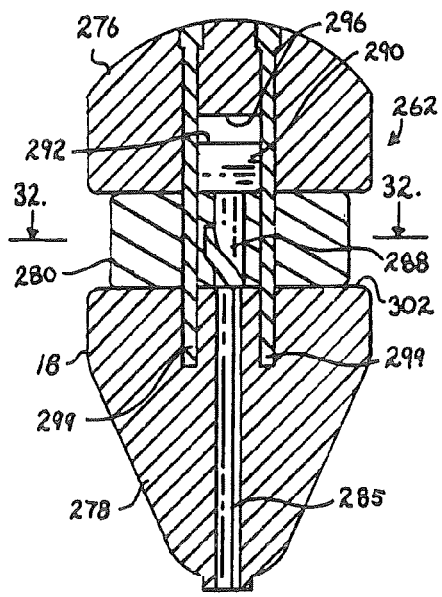
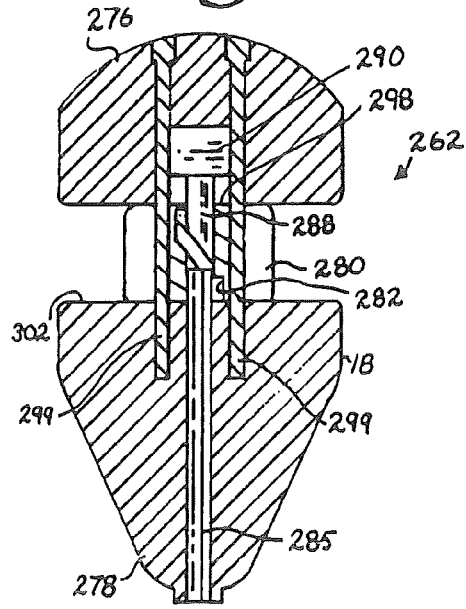
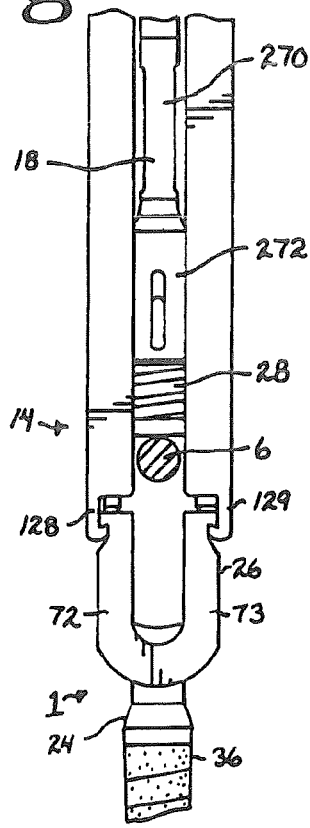
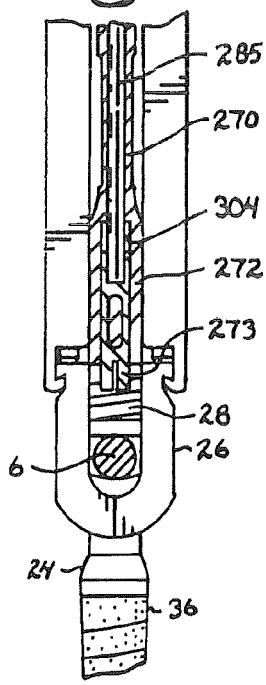
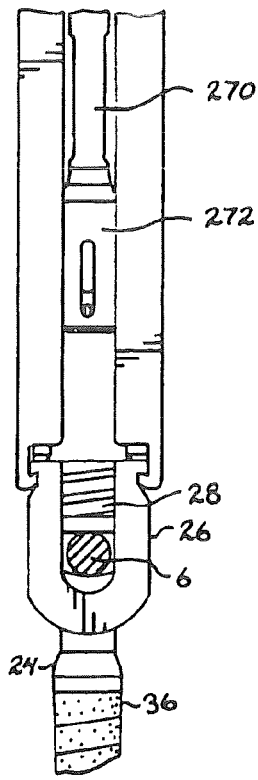

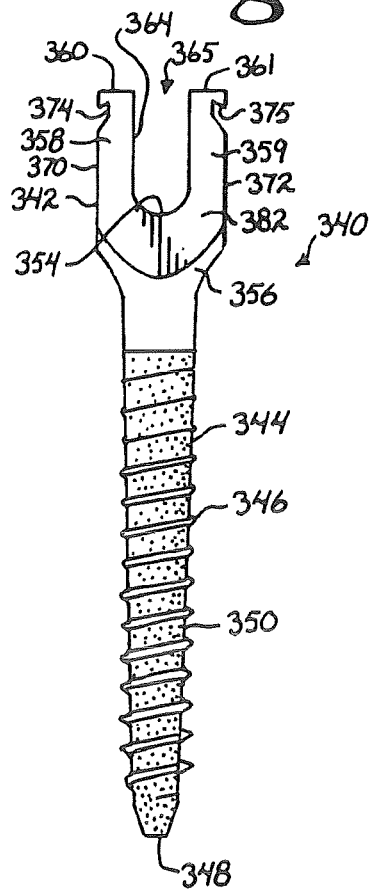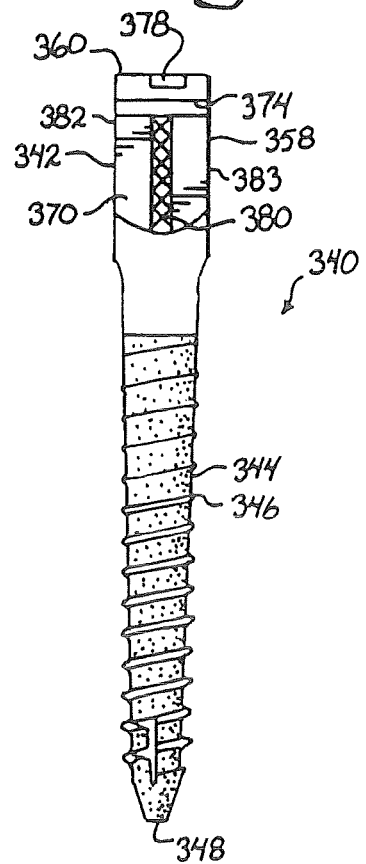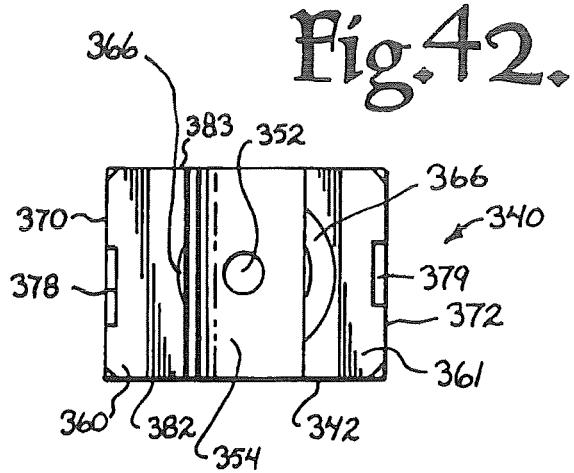

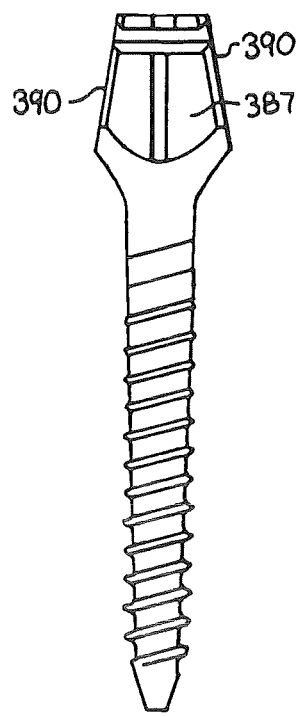
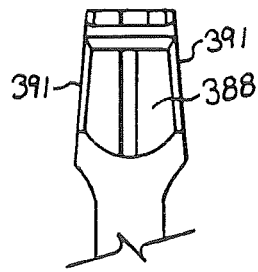
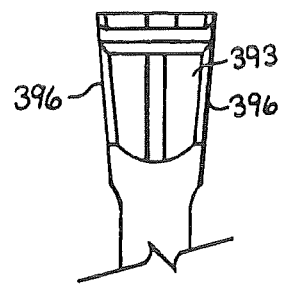
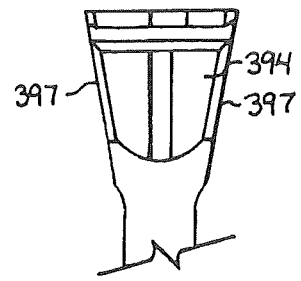

DYNAMIC SPINAL STABILIZATION ASSEMBLIES, TOOL SET AND METHOD

CROSS-REFERENCE TO RELATED APPLICATIONS

This application is a continuation of U.S. patent application Ser. No. 12/927,673, filed Nov. 19, 2010, now U.S. Pat. No. 9,216,039, which is a continuation of U.S. patent application Ser. No. 11/328,481, filed Jan. 9, 2006, now U.S. Pat. No. 7,862,587, that claims the benefit of priority to U.S. Provisional Application Nos. 60/722,300, filed Sep. 30, 2005; No. 60/725,445, filed Oct. 11, 2005; No. 60/728,912, filed Oct. 21, 2005 and No. 60/736,112, filed Nov. 10, 2005, all of which are incorporated herein by reference U.S. patent application Ser. No. 11/328,481 is a continuation-in-part of U.S. patent application Ser. No. 11/272,508, filed Nov. 10, 2005, now U.S. Pat. No. 9,050,148, that claims the benefit of U.S. Provisional Application No. 60/630,536 filed Nov. 23, 2004, and is a continuation-in-part of U.S. patent application Ser. No. 10/996,289, filed Nov. 23, 2004, now U.S. Pat. No. 8,152,810; and also is a continuation-in-part of U.S. patent application Ser. No. 10/789,149, filed Feb. 27, 2004, now U.S. Pat. No. 7,160,300 on Jan. 9, 2007; each of which are incorporated herein by reference.

BACKGROUND OF THE INVENTION

The present invention relates to apparatuses and methods for use in performing spinal surgery and, in particular, to bone attachment structures, bone attachment insertion and manipulation tools and methods of using such tools, especially for percutaneously implanting spinal screws and for implanting a dynamic stabilization connecting member for spinal support and alignment, using minimally or less invasive techniques.

For many years, spinal osteosynthesis apparatuses have been utilized to correct spinal deformities, injuries or disease. In such procedures, substantially rigid longitudinal connecting members, for example, elongate solid rods, are surgically attached to vertebrae of the spine to provide support and/or to realign or reposition certain vertebrae. The longitudinal connecting members are typically secured to vertebrae utilizing bone screws and other spinal implants. In order to reduce the impact of such surgery on the patient, a desirable approach is to insert such implants percutaneously or with surgical techniques that are less invasive to the body of the patient. In order to provide for protected motion with more normal or natural spinal flexibility, more flexible or dynamic longitudinal connecting members may be chosen over solid rigid rods.

Problems arise when implant deployment and insertion tools designed for traditional open surgery that is more invasive are utilized in percutaneous or less invasive surgery or with dynamic stabilization longitudinal connecting members. The tools may be bulky, oversized or have irregular surfaces or protrusions that can catch and traumatize tissues. A projecting actuator arm or fastening member may be useful with respect to the spinal screw implantation process or the rod reduction process, but there may be insufficient clearance to use such structure and/or such structure may produce additional unwanted trauma which the percutaneous surgery is attempting to avoid.

A percutaneous or less invasive procedure also presents a problem with implantation of elongate connecting members that have historically required a long incision and open wound in order to provide for the length of the connecting member and the space required for the surgeon's hands as well as the tools needed to manipulate the rod. Such problems are then compounded by the implants and insertion tools used with the connecting member.

Consequently, it is desirable to develop apparatuses and techniques that allow for the insertion of bone screws, the insertion and reduction of elongate connecting members into the bone screws and the securing of the connecting member to the bone screws with significantly less invasion into the body of the patient.

Historically, it also has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (flexion, extension and sideways), twisting (torsion), compression and distraction, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which more elastic materials and/or shapes are utilized for a longitudinal connecting member fixed between a pair of pedicle screws in an attempt to create, as much as possible, a more normal loading pattern between the vertebrae in flexion, extension, compression, distraction, side bending and torsion. Tools utilized with traditional rods or other more rigid structure may not be appropriate for manipulating more flexible connecting members and cooperating bone attachment structures. The dynamic conditions associated with spinal movement therefore provide a challenge not only for the design of elongate elastic longitudinal connecting members, but also for the design of cooperating bone attachment structure and tooling.

SUMMARY OF THE INVENTION

Bone attachment assemblies and cooperating tools for manipulating such assemblies according to the invention are provided for use in minimal or less invasive surgery, including dynamic spinal stabilization. An illustrated bone attachment and tool assembly for implanting a longitudinal connecting member in a patient includes at least two spinal implants, an insertion tool or tools, a bone screw driver and a connection or reduction tool.

Each spinal implant includes a receiver and a spinal attachment portion, the receiver having a channel for receiving a longitudinal connecting member. The receiver also has opposed sides with insertion tool attachment structure thereon and an inner surface with a first guide and advancement structure thereon sized and shaped to receive a closure structure. The opposed sides of the receiver have a planar surface and the tool attachment structure includes an undercut running substantially parallel to a top surface of the receiver sized and shaped for receiving projections on the insertion tool. The receiver opposed sides are substantially similar, and in some embodiments substantially parallel. In other embodiments, the opposed sides slope toward one another from near a bottom to the top of the receiver, forming a trapezoidal profile, the degree of slope corresponding to an actual or desired degree of segmental lordosis of a patient's spine. In other embodiments, the opposed sides slope away from one another from near a bottom to the top of the receiver, forming an inverted trapezoidal profile, the degree of slope corresponding to a degree of actual or desired kyphosis of a segment or segments of a patient's spine. Furthermore, spinal implants of the invention may be open or closed fixed bone anchors (hooks or screws), hinged bone screws, or polyaxial bone screws.

As stated above, the tool assembly further includes at least one insertion tool, and preferably an insertion tool for each bone anchor or attachment structure. The insertion tool has an elongate body with a top, a bottom, and opposed spinal implant engaging structure near the bottom of the body. The body further has a longitudinal axis, an outer surface and a channel with a lateral opening extending through the outer surface and along the longitudinal axis from a top to a bottom of the insertion tool. At least a portion of the channel opening is sized and shaped for receiving a longitudinal connecting member, the body further having an inner surface with a second guide and advancement structure disposed near the top. The insertion tool implant engaging structure is sized and shaped to engage the spinal implant tool attachment structure in only one orientation. A starting location of the second guide and advancement structure is positioned so as to cooperate with the first guide and advancement structure of the receiver for precise mating between a closure structure and the first guide and advancement structure and placement of the closure structure at an exact location within the receiver.

Tool assemblies according to the invention also include at least one driver having a handle, a stem receivable in the insertion tool and a driving end configured for rotatable engagement with the spinal implant. Furthermore, the driver has at least one laterally extending tab sized, shaped and located for engagement with the insertion tool at a surface defining the lateral opening of the channel. In the illustrated embodiment, the insertion tool lateral opening includes at least a narrow opening near the top and also a through channel. The driver tab extends through the narrow opening when the driver is received by the insertion tool with the driving end engaging a spinal implant. The driver further includes a second tab extending laterally from the through channel when the driver is received by the insertion tool with the driving end engaging a spinal implant. The driver is sized and shaped to fit snugly within a U-shaped channel formed by opposed arms of the spinal implant.

Tool assemblies of the invention further include at least one reduction tool having a handle, a stem receivable in the insertion tool and a retractable driving tip sized and shaped for holding a closure structure thereon in only one orientation. The stem includes a third guide and advancement structure sized and shaped to mate under rotation with the second guide and advancement structure of the insertion tool.

Furthermore, according to the invention closure structures are provided, each having a fourth guide and advancement structure sized and shaped to mate with the first guide and advancement structure of the receiver. Each closure structure has an internal drive for receiving the reduction tool driving tip, the internal drive having a key slot for receiving the reduction tool driving tip in only one location.

A hinged spinal implant according to the invention for fixing a longitudinal connecting member to the spine includes a receiver having a pair of opposed arms defining an open channel sized and shaped to receive a longitudinal connecting member. The receiver further has a central bore and a lower opening, the bore communicating with both the U-shaped channel and the lower opening. The implant includes a shank having an elongate body and an upper end integral with the body. The upper end has a top surface sized and shaped for frictional engagement with the longitudinal member. The upper end also has a projection disposed substantially perpendicular to the elongate body, the projection sized and shaped to be received between the arms and slidingly mate with a receiver surface defining a portion of the open channel, putting the shank in hinged relationship with the receiver, articulating in a plane that includes the pair of opposed arms when the projection engages the receiver surface with the shank body extending through the lower opening. In the illustrated embodiment, the receiver channel is U-shaped and the projection is a first projection, with the shank upper end having a second projection extending in a direction opposite the first projection, the first and second projections each having a U-shaped surface. Furthermore, the receiver surface and the first and second projections have cooperating teeth for locking the shank into a selected angular position with respect to the receiver. In one embodiment, the shank is up-loadable into the receiver through the lower opening. In another embodiment, the shank is downloadable into the receiver through the channel. It is also foreseen that the shank need not be an integral one piece structure.

A dynamic vertebral support connecting member implantation kit according to the invention, adapted for use with a plurality of vertebrae, includes a plurality of hinged, polyaxial or monoaxial bone screws and hooks, each bone anchor being adapted for implantation in or on one vertebra, each of the implants having structure for attachment to an insertion tool in only one orientation. The kit also includes a plurality of insertion tools, at least one driver, and at least one reduction tool having a retractable tip for holding a closure structure. Other tools may be included in the kit such as, but not limited to a closure starter. Also provided in the kit are a plurality of closure structures having a key slot or other structure such that the closure structures may be held by the reduction tool in only one orientation.

A method according to the invention includes the steps of providing at least first and second insertion tools, each tool releasably attachable to a bone screw or hook, each end guide tool having an elongate channel with a lateral opening extending the length, at least a portion of the opening for receiving a longitudinal connecting member, an inner surface of the tool having a guide and advancement structure thereon with a starting location placed for exact mating and placement of a closure structure within a bone screw or hook.

The method further includes attaching each insertion tool to a bone screw, for example, and inserting a driving tool into the insertion tool channel with or without a tab of the driving tool extending through the insertion tool lateral opening, followed by driving the bone screw into a vertebra by rotating the driving tool, insertion tool and bone screw assembly. Then, a longitudinal connecting member is inserted into the lateral openings of each insertion tool.

The method also includes providing a closure structure for each bone screw, each closure structure having a drive structure sized and shaped for releaseable attachment to a reduction tool. Also, the method includes providing a reduction tool having a retractable driving tip sized and shaped to hold a closure structure in only one orientation, the reduction tool also having a guide and advancement structure thereon sized and shaped to mate with the guide and advancement structure on the insertion tool. The reduction tool with attached closure structure is inserted into the channel of the insertion tool and rotated, driving the longitudinal connecting member downward into the bone screw and rotating the closure structure into precise mating engagement with the bone screw.

OBJECTS AND ADVANTAGES OF THE INVENTION

Therefore, the objects of the present invention are: to provide a compact tool assembly for supporting and installing bone attachment structures, such as bone screws, hooks and dynamic stabilization connecting members and other spinal implants with minimal or less surgical invasion to the patient; to provide both hinged and fixed open bone screws and hooks for cooperation with dynamic stabilization connecting members; to provide open and closed lordosing and kyphosing implants (screws and hooks) for use in such an assembly; to provide a set of tools for implanting a dynamic spinal fixation connecting member for support or alignment along a human spine with minimal or less surgical invasion of the patient; to provide such a set of tools including an insertion tool, driving, reduction and manipulation tools for use in implanting a bone attachment implant, directing a longitudinal connecting member downwardly into such an implant and capturing the longitudinal connecting member within a receiver of the bone attachment implant; to provide such a set of tools including a closure reduction and installation tool for securing the dynamic fixation connecting member to the bone attachment implant; to provide such a set of tools wherein the insertion, driving and manipulation tools are easily attached to and disengaged from the bone attachment implants; to provide such a set of tools wherein the insertion tools, supports or stabilizers, deployment tools, reduction tools, bone implant installation tools and closure installation tools are all easily aligned, positioned, and engaged, if necessary, with respect to the bone implants and are disengaged from the bone implants and other tools in the installation assembly by manual manipulation of the surgeon; to provide a method of implanting a dynamic stabilization connecting member into bone implants within a patient with minimal or less surgical invasion of the patient; to provide such a method utilizing the previously described tools for implantation of such a connecting member; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a hinged bone screw assembly according to the present invention having a shank, a receiver and shown with a closure structure.

FIG. 2 is an enlarged cross-sectional view of the shank taken along the line 2-2 of FIG. 1.

FIG. 3 is an enlarged top plan view of the receiver of FIG. 1.

FIG. 4 is an enlarged side elevational view of the receiver of FIGS. 1 and 3.

FIG. 5 is an enlarged top plan view of the closure structure of FIG. 1.

FIG. 6 is an enlarged cross-sectional view of the receiver taken along the line 6-6 of FIG. 1 and the shank of FIG. 1 in partial front elevation, showing an initial stage of attachment of the shank to the receiver.

FIG. 7 is an enlarged cross-sectional view of the receiver taken along the line 6-6 of FIG. 1 and the shank of FIG. 1 in partial side elevation, rotated ninety degrees and lowered into a seated position within the receiver.

FIG. 8 is an enlarged cross-sectional view, similar to FIG. 7, further showing the shank in cross-section along the line 8-8 of FIG. 1, with the shank disposed at an angle with respect to the receiver and further showing an extent of articulation in phantom.

FIG. 9 is an enlarged perspective view of first and second hinged bone screws according to FIG. 1 shown with a longitudinal connecting member in the form of a cord and cord receiving spacer.

FIG. 10 is an exploded and partial front elevational view of a tool assembly according to the present invention showing a lock pin, an insertion tool and the bone screw of FIG. 1.

FIG. 11 is a top plan view of the insertion tool of FIG. 10.

FIG. 12 is a cross-sectional view taken along the line 12-12 of FIG. 10.

FIG. 13 is a bottom plan view of the insertion tool of FIG. 10.

FIG. 14 is a side elevational view of the insertion tool of FIG. 10.

FIG. 15 is a cross-sectional view taken along the line 15-15 of FIG. 14.

FIG. 16 is a partial cross-sectional view taken along the line 16-16 of FIG. 15.

FIG. 17 is a partial cross-sectional view taken along the line 17-17 of FIG. 15.

FIG. 18 is an enlarged and partial view of the insertion tool of FIG. 10 with portions broken away to show the detail thereof.

FIG. 19 is an enlarged front elevational view of a lock pin driver according to the invention shown mounted on a lock pin installed to the insertion tool of FIG. 10, shown in partial front elevation.

FIG. 20 is an enlarged top plan view of the lock pin driver of FIG. 19.

FIG. 21 is an enlarged bottom plan view of the lock pin driver of FIG. 19.

FIG. 22 is a cross-sectional view taken along the line 22-22 of FIG. 20.

FIG. 23 is an enlarged and partial front elevational view of the insertion tool and bone screw of FIG. 10, showing the bone screw attached to the insertion tool and with two lock pins.

FIG. 24 is an enlarged and exploded front elevational view of a bone screw driver according to the invention and the insertion tool and attached bone screw of FIG. 23.

FIG. 25 is an enlarged bottom plan view of the driver of FIG. 24.

FIG. 26 is an enlarged and partial side elevational view of the driver of FIG. 24.

FIG. 27 is an enlarged and exploded front elevational view of a reduction tool according to the invention and the insertion tool and attached bone screw of FIG. 24, also shown with the closure structure of FIG. 1 and a longitudinal connecting member.

FIG. 29 is an enlarged and partial front elevational view similar to FIG. 27, showing the reduction tool received in the insertion tool and engaged with the closure structure.

FIG. 30 is an enlarged and partial front elevational view of an upper portion of the reduction tool of FIG. 28 with portions broken away to show the detail thereof, a driving shaft being shown in an extended position.

FIG. 31 is an enlarged and partial front elevational view of the upper portion of the reduction tool of FIG. 27 with portions broken away to show the detail thereof, the driving shaft being shown in a retracted position.

FIG. 33 is an enlarged and partial front elevational view of a lower portion of the reduction tool of FIGS. 27 and 30, shown engaged with the closure structure and reducing a longitudinal connecting member along the insertion tool of FIG. 27 and toward the attached bone screw.

FIG. 34 is an enlarged and partial front elevational view similar to FIG. 33 with portions broken away to show the detail thereof and further showing the closure structure fully seated in the bone screw.

FIG. 35 is an enlarged and partial front elevational view similar to FIGS. 33 and 34, further showing the reduction tool in the retracted position of FIG. 31 and being moved away from a fully seated bone screw.

FIG. 40 is a front elevational view of a first alternative monoaxial bone screw according to the invention having an open receiver.

FIG. 41 is a side elevational view of the bone screw of FIG. 40.

FIG. 42 is a top plan view of the bone screw of FIG. 40.

FIG. 43 is a side elevational view of a second alternative monoaxial bone screw according to the invention having an open receiver and trapezoidal profile.

FIG. 44 is a partial side elevational view of a third alternative monoaxial bone screw according to the invention having an open receiver and trapezoidal profile.

FIG. 45 is a partial side elevational view of a fourth alternative monoaxial bone screw according to the invention having an open receiver and reverse trapezoidal profile.

FIG. 46 is a partial side elevational view of a fifth alternative monoaxial bone screw according to the invention having an open receiver and reverse trapezoidal profile.

DETAILED DESCRIPTION OF THE INVENTION

Figure 32:
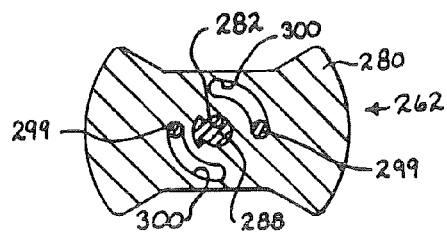
FIG. 32 is an enlarged cross-sectional view taken along the line 32-32 of FIG. 30.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-38, the reference numeral 1 generally designates a hinged bone screw for cooperation with a dynamic stabilization connecting member, generally 3, such as the illustrated cord 6 with cannulated spacers 8. The spacers 8 are substantially cylindrical with opposed planar sides 9. Tools for implanting a bone screw 1 on a vertebra 10 of a human spine 12 and manipulating cooperating bone screws 1 and longitudinal connecting members 3 may include one or more insertion tools, generally 14, a bone screw driver 16, a reduction tool 18, and a closure starter 20.

The hinged bone screw assembly 1 includes a shank 24 and a receiver 26. A closure structure 28 is further included for engagement with the receiver to capture and fix the cord 6 of the longitudinal connecting member 3 within the receiver. The shank 24 further includes a body 36 integral with an upwardly extending end portion 38. The shank 24 and the receiver 26 are assembled prior to implantation of the shank body 36 into the vertebra 10. It is noted that any reference to the words top, bottom, up and down, and the like, in this application refers to the alignment shown in the various drawings, as well as the normal connotations applied to such devices, and is not intended to restrict positioning of the bone screw assembly 1 and tools 14, 16, 18 and 20 in actual use.

The shank 24 of the bone screw assembly 1, best illustrated in FIGS. 1, 2 and 6-9, is elongate, having an axis of rotation A. The shank body 36 has a helically wound, radially outwardly extending bone implantable thread 40 axially extending from near a lower end or tip 44 of the body 36 to near a slanted or sloped surface 46 that is adjacent to a smooth substantially cylindrical surface 48 located adjacent to the end portion 38. During use, the body 36 utilizing the thread 40 for gripping and advancement is implanted into the vertebra 10 leading with the tip 44 and driven down into the vertebra 10 with the driving tool 16 so as to be implanted in the vertebra 10 to near the sloped surface 46.

To provide a biologically active interface with the bone, an outer surface 50 of the shank body 36 that includes the thread 40 and extends between the surface 46 and the tip 44 is coated, perforated, made porous or otherwise treated 52. The treatment 52 may include, but is not limited to a plasma spray coating or other type of coating of a metal or, for example, a calcium phosphate; or a roughening, perforation or indentation in the surface 50, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

The sloped surface 46 extends radially inward and axially upward from the shank body 36 to the cylindrical portion 48. Further extending laterally outwardly from the cylindrical portion 48 is the upper end portion 38 that provides a connective or capture apparatus disposed at a distance from the threaded shank body 36 and thus at a distance from the vertebra 10 when the body 36 is implanted in the vertebra 10. The upper end portion 38 is configured for connecting the shank 24 to the receiver 26 and capturing the shank 24 in the receiver 26. The upper end portion 38 has a pair of projections or wings 56 that extend laterally oppositely outwardly from the cylindrical surface 48. Each projection 56 has a lower curved, convex surface 57 with ridges or locking teeth 58 sized and shaped to engage a concave toothed surface of the receiver 26, to be described more fully below. The locking teeth 58 are sized and shaped to provide locking positions at about every ten degrees for a total range of hinged motion of about sixty degrees, about thirty degrees on either side of a central axis B of the receiver 26 as illustrated in FIG. 8. The upper or end portion 38 further includes a top surface 60 that includes a concave portion sized and shaped for receiving and engaging the driver 16 as will be described more fully below and also the cord 6. A side surface 62 extends between the top surface 60 and each curved lower surface 57.

In the illustrated embodiment, the shank 24 is cannulated with a small central bore 66 extending an entire length of the shank along the axis A. The bore 66 is coaxial with the threaded body 36 and opens at the tip 44 and the top surface 60, providing a passage through the shank interior for a length of wire or pin inserted into the vertebra 10 prior to the insertion of the shank body 36, the wire or pin providing a guide for insertion of the shank body 36 into the vertebra 10.

With reference to FIGS. 1, 3, 4 and 6-8, the receiver 26 includes a base 70 integral with a pair of opposed upstanding arms 72 and 73 that extend from the base 70 to respective top surfaces 74 and 75. The arms 72 and 73 form a U-shaped cradle and define a U-shaped channel 76 between the arms 72 and 73 and include an upper opening 77 and a lower seat 78. The lower seat 78 includes locking teeth 80 sized and shaped to engage the locking teeth 58 of the shank upper end portion 38. Each of the arms 72 and 73 has an interior surface that defines an inner cylindrical profile and includes a discontinuous helically wound guide and advancement structure 82. In the illustrated embodiment, the guide and advancement structure 82 is a partial or discontinuous helically wound flangeform configured to mate under rotation with a similar structure on the substantially cylindrical closure structure 28, as described more fully below. However, it is foreseen that the guide and advancement structure 82 could alternatively be a buttress thread, a square thread, a reverse angle thread or other thread like or non-thread like helically wound advancement structures for operably guiding under rotation and advancing the closure structure 28 downward between the arms 72 and 73 and having such a structural nature as to resist splaying of the arms 72 and 73 when the closure 28 is advanced into the U-shaped channel 76 and tightened.

Each of the arms 72 and 73 has a substantially planar outer surface 84 and 85, respectively, that includes a substantially linear undercut tool engagement groove 86 and 87, respectively, V-shaped in cross-section and formed in the receiver 26 near the respective top surfaces 74 and 75. Sloping surfaces 88 and 89 run inwardly and upwardly from the respective outer surfaces 84 and 85 to the respective grooves 86 and 87. The V-shaped grooves 86 and 87 secure the insertion tool 14 to the bone screw receiver 26 during implantation of the screw into bone and manipulation of the longitudinal connecting member 3 and closure structure 28, and in cooperation with the sloping surfaces 88 and 89, allows for easy, sliding release of the tool 14 from the bone screw during removal of the tool at the end of the procedure. The grooves 86 and 87 cooperate with projections of the insertion tool 14, which will be described in greater detail below, the insertion tool projections being received in the grooves 86 and 87 during implantation of the shank body 36 into the vertebra 10 and subsequent installation of the connecting member 3 and closure structure 28. Upper ledges 90 and 91 adjacent to top surfaces 74 and 75, respectively, extend laterally from the respective receiver surfaces 84 and 85 and from a substantially planar side 92 to an opposite planar side 93, partly defining the respective undercut grooves 86 and 87. Each ledge 90 and 91 includes a narrow opening or slit 94 and 95, respectively, formed therein and running from the top surface 74 and 75 to respective side surfaces 84 and 85. The slits 94 and 95 run parallel with the axis B of the receiver. The ledges 90 and 91 are substantially similar in size and shape with the exception of the position and size of the slits 94 and 95. The slit 94 is located substantially centrally in the ledge 90 while the slit 95 is substantially off-center and also wider than the slit 94, such width measured in a direction perpendicular to the axis B. As will be described more fully below, the slits 94 and 95 cooperate with projections on the insertion tool 14 and cooperate and attach to the tool 14 in only one location and thus there is only one way in which to orient and attach the tool 14 to the receiver 26. It is foreseen that the slits 94 and 95 may be of a variety of sizes and shapes with cooperating structure on the insertion tool 14 such that the tool 14 will only attach to the receiver 26 in a single position or orientation, resulting in a desired precise alignment between the bone screw 1, the insertion tool 14 and thereafter, the reduction tool 18. The receiver arm outer side surface 72 further includes a laser or otherwise etched alignment stripe 98 running parallel to the axis B. The stripe 98 corresponds to a similar stripe 100 on the insertion tool 14 (illustrated in FIGS. 38 and 39), providing a visual aid and ease in the alignment and proper attachment of the insertion tool 14 with the receiver 26 by aligning the stripe 98 with the stripe 100.

Communicating with the U-shaped channel 76 and located within the base 70 of the receiver 26 is a chamber or cavity 102 that opens upwardly into the U-shaped channel 76 and communicates and opens downwardly to an oblong lower opening or neck 104 in the base 70. The lower opening 104 communicates with an outer lower exterior or bottom 105 of the base 70. The base lower opening 104 and the cavity 102 are sized and shaped to receive the upper end portion 38 of the shank 24 as illustrated in FIG. 6. The cavity 102 is defined in part by upper ceiling or stop surfaces 106 disposed on either side of the channel 76, the surfaces 106 prohibit the end portion 38 from being advanced through the channel 76 to the receiver upper opening 77 when the upper portion 38 is in a loading orientation, receivable in the oblong lower opening 104. The cavity 102 is also partially defined by opposed inner surfaces 107 that extend from the opening 104 to the upper surfaces 106. As will be described in further detail below, to seat the upper portion 38 in the receiver 26, the upper portion 38 is slid upwardly along the surfaces 107, then rotated ninety degrees about the receiver axis B within the cavity 102 and thereafter lowered toward the opening 104 as illustrated in FIG. 7 to seat the upper end portion 38 curved surface 57 on the receiver lower seat 78, with the teeth 58 engaging the teeth 80. The cavity 102 is sized and shaped to accommodate the rotation of the wing projections 56 of the upper end portion 38 about the axis B. Once rotated, the neck 104 is sized and shaped to have a width that is smaller than the shank upper portion 38 measured along the wing projections 56 so as to form a restriction at the location of the neck 104 relative to the winged upper portion 38, to prevent the upper portion 38 from passing from the cavity 102 and out into the lower exterior 105 of the receiver 26 when the upper portion 38 is seated on the lower seating surface 78. Communication between the curved surface 57 and the lower seat 78 allow for articulated or hinged motion of the shank 24 with respect to the receiver 26 in a single plane as illustrated in FIG. 8, with the teeth 58 and 80 providing for fixed engagement between the shank 24 and the receiver 26 when a force is placed on the shank end portion 38 by rotating and torquing the closure structure 28 against the cord 6 of the longitudinal connecting member 3. The hinged motion of the shank 24 is limited by the cylindrical surface 48 of the shank 24 abutting the oblong neck 104 near either outer side 84 and 85 of the receiver 26.

With particular reference to FIG. 9, the illustrated longitudinal connecting member 3 includes from one up to a plurality of cannulated spacers 8 sized and shaped to receive the cord 6 therethrough. The spacers 8 are also sized and shaped to fit between pairs of bone screws 1, cooperating with the cord 6 to support adjacent vertebrae when implanted between bone screws 1. The spacers 8 may be made of a variety of materials including metals, plastics and composites. The illustrated spacer is made from a plastic, such as polycarbonate-urethane. The illustrated cord is also made from plastic, such as polyethylene-terephthalate. The spacer/cord combination provides for a flexible anatomical holding and control of the spinal motion segment or segments to be treated. It is also foreseen that other longitudinal connecting members may be utilized with the bone screws or other implants according to the invention, including solid rods and dynamic stabilization connecting members and member assemblies including, but not limited to coils, springs, and coil or spring and rod combinations including coils having rod-like inserts. Such connecting members can provide for protected motion, including torsional elasticity and elastic axial compression and distraction in addition to flexibility.

The closure structure 28 closes between the spaced bone screw arms 72 and 73 to secure the connecting member 3 in the channel 76. The closure structure 28 can be any of many different plug type closures. With particular reference to FIGS. 1 and 5, the illustrated closure structure 28 has a cylindrical body 108 that has a helically wound mating guide and advancement structure 110. The illustrated guide and advancement structure 110 is a helically wound flange-form that interlocks with a reciprocal flangeform of the guide and advancement structure 82 of the receiver 26. However, it is foreseen that as with the guide and advancement structure 82, the structure 110 can be of any type, including V-type threads, buttress threads, reverse angle threads, or square threads, that cooperate with the guide and advancement structure 82 on the bone screw arms 72 and 73. A suitable flangeform locking guide and advancement structure is disclosed in U.S. Pat. No. 6,726,689, which is incorporated herein by reference.

The closure structure 28 further includes a top surface 112 and a substantially planar bottom surface 113, the bottom surface 113 providing a smooth contact surface for engagement with a cord 6 of the longitudinal connecting member 3. Formed in the top surface 112 is a substantially hex-shaped internal drive socket or aperture 115, further including a key slot 116 for precise and particular engagement with the reduction tool 18 as will be described in further detail below. Although a hex-shaped drive 115 is illustrated herein, it is foreseen that the closure structure internal drive may be of other shapes or sizes. Alternatively, the closure structure 28 may include an external driving head that breaks away from the cylindrical body 102 upon the application of a preselected torque.

The insertion tool 14 is best illustrated in FIGS. 10-18. In particular, the tool 14 has an elongate body 118 and two cooperating lock pins 120. The elongate body 118 has an axis of rotation C and is sized and shaped to be sufficiently long to extend from an implanted bone screw 1 through an exterior of a patient's skin so as to provide an outwardly extending and upper handle portion 122 that allows and provides for gripping by a surgeon during procedures utilizing the insertion tool 14, with or without a driver 16, a reduction tool 18 or a closure starter 20. The insertion tool 14 further includes an intermediate portion 124 and a lower implant engaging portion 126 which includes opposed implant engaging members or tangs 128 and 129 for securing a bone screw 1 or other implant there between.

Figure 38:
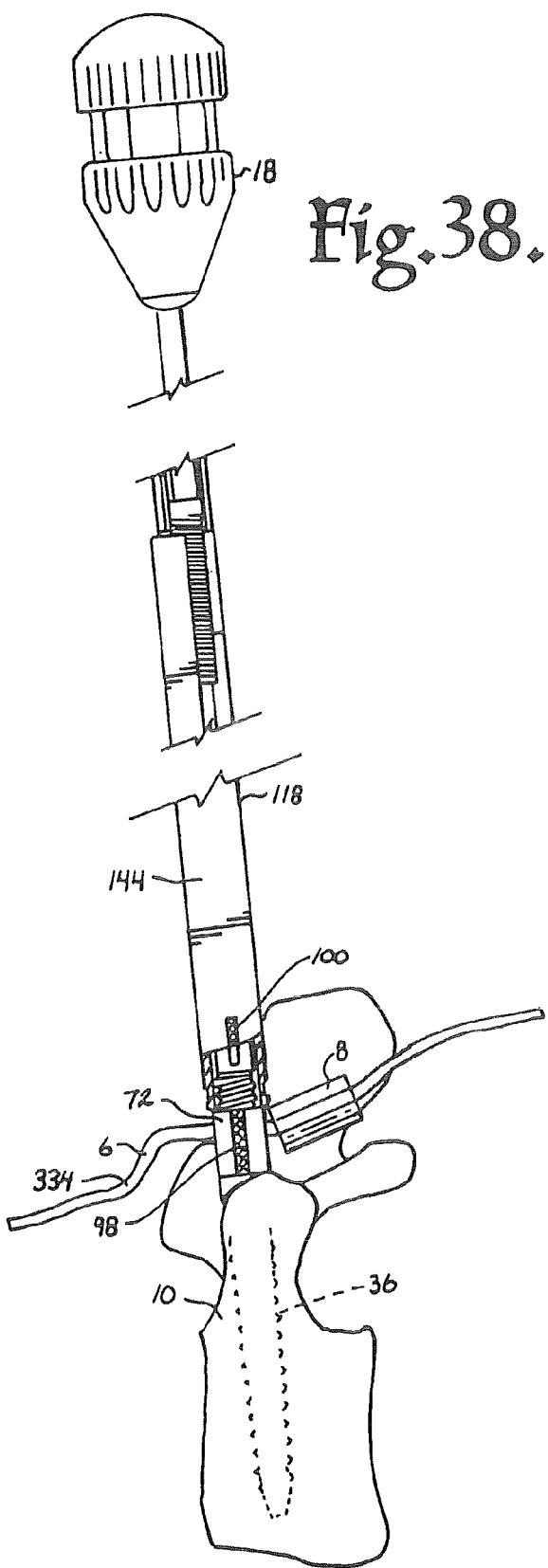
FIG. 38 is a partial and generally schematic view of a patient's spine, showing an implanted bone screw with attached insertion tool receiving a reduction tool engaged with a closure structure.
Figure 39:
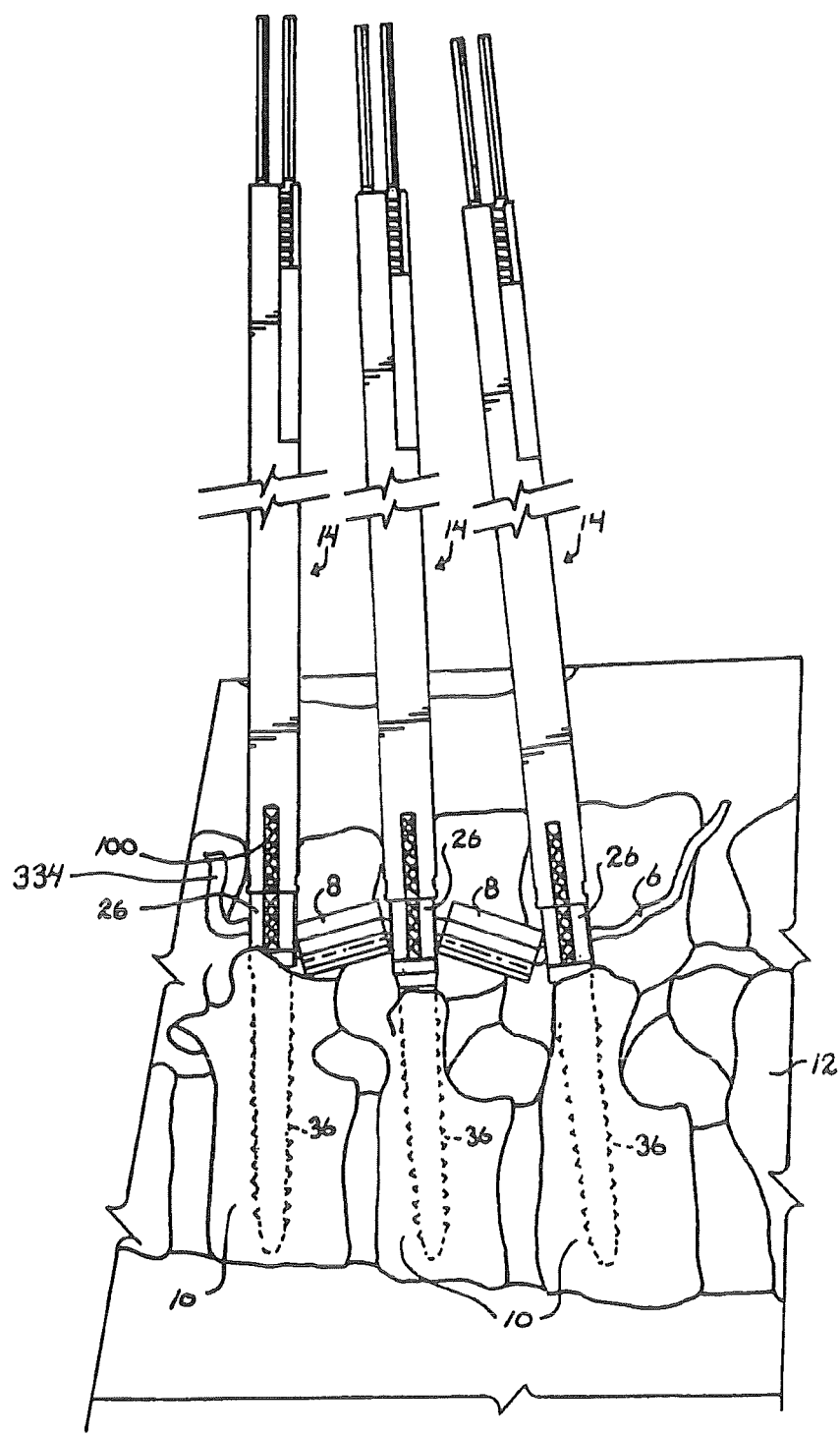
FIG. 39 is a partial and generally schematic view of a patient's spine, showing three insertion tools, each attached to an implanted bone screw and further showing a stage of implantation of a cord and threaded spacers.

With reference to FIGS. 11-13, the insertion tool 14 has a generally rectangular shape when viewed on end or in a cross section taken perpendicular to the axis of rotation C. The tool 14 further forms an open channel 132 running along the axis C from a top surface 134 to bottom surfaces 136 thereof. The channel 132 is substantially defined by an inner discontinuous cylindrical wall 138. The wall 138 is sized and shaped to receive the driving and manipulating tools 16, 18 and 20 as will be described in greater detail below. The tool 14 further includes a front 140 and opposed back 142, and opposed sides 144 and 146 that attach the front 140 to the back 142. The back 142 includes an upper substantially solid wall portion 147. With reference to FIGS. 38 and 39, the side 144 includes the laser etched alignment stripe 100 that aids a surgeon in properly aligning and mating the tool 14 with the receiver 26 by simply aligning the stripe 100 with the stripe 98 that is located on only one side 84 of the receive 26. As illustrated in FIG. 14, the side 146 is substantially planar and solid and is integrally joined to the front 140 and the back 142 substantially along a length thereof parallel to the axis C. The opposite side 144 is integral to the back 142 substantially along an entire length thereof parallel to the axis C. The side 144 is also integral with the front 140 along the intermediate 124 and lower 126 portions of the tool 14. It is foreseen that the cross-sectional shape of the tool 14 could be rounded or some other shape.

A through channel 148 is formed in both the front 140 and the back 142 portions of the tool 14 and communicates with the longitudinal channel 132. The openings and channels described herein with respect to the tool 14 are sized and shaped to receive and allow passage of both tools and implants as will be described more fully below. The through channel 148 begins near the upper handle portion 122 and extends through the bottom surfaces 136 of the tangs 128 and 129 that define a lower portion of the channel 148 and the lower, implant engaging portion 126 of the tool 14.

With respect to the axis C, the beginning of the through channel 148 near the upper portion 122 is of a staggered arrangement. A squared off, discontinuous and off-center opening 149 is formed in the front 140 opposite the solid portion 147 of the back 142, the opening 149 partially defined by a first corner 150 formed in the front 140 and a second corner 151 formed in the side 144, the opening 149 communicating with an upper more narrow channel 152 that extends from the opening 149 through the top surface 134. The opening 149 then extends along the front 140 all the way through the bottom surfaces 136 of the tool 14, communicating with the open longitudinal channel 132. As will be discussed more fully below, the opening 149 is sized and shaped to readily receive a driving end of the bone screw driver 16, the lower housing and retractable driving tip of the reduction tool 18 and the tip of the closure starter 20, as well as the entire closure structure 28. The lateral opening of the narrow channel 152 is sized and shaped to receive slender shafts of the driver 16, reduction tool 18 and closure starter 20. Thus, the opening 149 communicating with both the narrow channel 152 and the through channel 148 provides for a continuous lateral or side opening along an entire length of the tool 14 along the axis C that is sized and shaped to receive longitudinal connecting members including, but not limited to cords 6, coils and rods, as well as closure implants and various manipulating tools. Near the corner 150, the opening 149 also is partially defined by a cut-out portion of the front 140 that exposes the side 144 of the tool 14. The opening 149 includes an elongate wall 154 in the side 144 that faces toward the front 140 and a lower or base surface 155 that runs perpendicular to the axis C. Above the corner 150, the wall 154 widens to form an upper portion 156 that extends to the top 134 of the tool 14, the upper portion 156 partially defining the upper narrow channel 152.

At the back 142 of the tool 14, a U-shaped opening 157 formed in the upper back portion 147 marks the beginning of the through channel 148 that extends through the back 142 and downwardly through the bottom surfaces 136. Thus, the through channel 148 that extends through the front opening 149 and the back opening 157, begins at the U-shaped opening 157 and is substantially uniform in width measured perpendicular to the axis C over the intermediate 124 and lower 126 portions of the tool 14, being substantially defined by the sides 144 and 146 that end in the tangs 128 and 129. The through channel 148 thus provides for some flexibility to allow for outward splaying of the tangs 128 and 129 near the bottom surfaces 136 and about the receiver 26 of the bone screw shank 1 as will be described in greater detail below.

With particular reference to FIGS. 11-13 and 18, near the intersection of the front 140 and the side 146, a narrow cylindrical side channel 158 is formed in the tool 14, running parallel to the axis C and partially defined by a threaded inner wall 160, the channel 158 and threaded wall 160 sized and shaped to rotatingly receive a first lock pin 120. At an opposite corner of the tool 14 at the intersection of the back 142 and the side 144, a second narrow cylindrical side channel 162 is formed in the tool 14, parallel to the axis C and having a threaded inner wall 164, the channel 162 and threaded wall 164 also sized and shaped for rotatingly receiving a lock pin 120. The channels 158 and 162 are open at both ends 134 and 136, with the threaded portions 160 and 164 being located near the top 134 in the upper portion 122 of the tool 14.

Also near the top 134 and within the upper portion 122 of the tool 14 is a discontinuous guide and advancement structure 168 disposed on the inner cylindrical wall 138 defining the central channel 132. The guide and advancement structure 168 is a substantially square thread sized and shaped to receive a cooperating guide and advancement structure of the reduction tool 18 to be described more fully below. A starting location 170 of the guide and advancement structure 168 on the insertion tool 14 is coordinated with a starting position of the guide and advancement structure on the reduction tool 18 and a starting location of the guide and advancement structure 82 of the bone screw receiver 26 when attached to the insertion tool 14, so as to provide for exact closure structure alignment and engagement within the receiver 26 to a specific, fully seated position, as also will be described more fully below.

The front 140 of the tool 14 includes two outer front faces 172 and 173 that are substantially similar in size and are spaced from one another, with the through channel 148 extending therebetween. The face 172 begins adjacent to the bottom 155 of the cut-out portion of the opening 149 and extends to the bottom surface 136. The face 173 extends an entire length of the tool along the axis C. The face 173 widens at an upper or top portion 175 of the front 140. The portion 175 partly defines the narrow channel 152 and supports the guide and advancement structure 168.

Near the bottom surfaces 136, both the faces 172 and 173 include a cut-out or recess 178 that extends into the sides 144 and 146, respectively, and is defined in part by the tangs 128 and 129, respectively. With particular reference to FIG. 23, the cut-outs 178 are each defined by an upper surface 180 disposed perpendicular to the axis C, an inner planar surface 182 disposed parallel to the axis C and a substantially planar lip surface 184 disposed at an acute angle with respect to the surface 182. The lip surface 184 is on each of a pair of opposed projections or implant engaging members 186 and 187, disposed on respective tangs 128 and 129, each projecting toward the axis C and sized and shaped to engage and slidingly fit within the grooves 86 and 87 respectively, of the receiver 26.

With particular reference to FIGS. 16 and 17, the inner surface 182 disposed above the projection 186 further includes a raised strip or projection 194 that runs parallel to the axis C and is sized, shaped and positioned to slidingly engage with the slit 94 in the ledge 90 of the arm 72 of the receiver 26. The inner surface 182 disposed above the projection 187 further includes a raised strip or projection 195 that also runs parallel to the axis C and is sized, shaped and positioned to slidingly engage with the slit 95 in the ledge 91 of the arm 73 of the receiver 26. As will be described in greater detail below and with reference to FIG. 23, the cooperation between the strip 194 and the slit 94 and the strip 195 and the slit 95 ensures proper alignment and mating of the insertion tool 14 and the receiver 26 and further prohibits front to back movement of the receiver 26 with respect to the insertion tool 14 when the tool 14 is mounted on the receiver 26 and the lock pins 120 contact respective top surfaces 74 and 75 of the receiver 26.

Each lock pin 120 is elongate, having a top surface 200 a curved bottom surface 202, a hex-shaped upper driving portion 204 disposed near the top surface 200 and a threaded portion 206 disposed near the driving portion 204 and on a smooth cylindrical body portion 207 of the lock pin 120. The smooth body portion 207 extends from the driving portion 204 to the bottom surface 202. As illustrated in FIG. 10, near the bottom surface 202, the body portion 207 may be of slightly reduced diameter as shown by the portion 208 to result in the bottom surface 202 being of a size and shape to fully contact the receiver 26 without overhang. The lock pin 120 is sized and shaped to be received in either of the cylindrical channels 158 and 162 in the insertion tool 14, with the threaded portion 206 rotatably receivable in either of the threaded inner walls 160 and 164. The lock pin 120 is sized and shaped to extend along and completely through either of the channels 158 and 162 until the curved bottom 202 abuts the top surface 74 or 75 of the receiver 26 with the upper driving portion 204 extending above the top 134 of the insertion tool 14 as illustrated, for example, in FIGS. 19 and 24.

The lock pins 120 are rotated and driven downwardly into the insertion tool 14 by a lock pin driver 210 illustrated in FIGS. 19-22. The lock pin driver 210 includes a substantially cylindrical elongate body 212 having an axis of rotation D and shown with outer grooves 214 to aid a surgeon in handling and rotating the driver 210. The driver further includes an upper projection or extension 216 that may be used to spread the tangs 128 and 129 of the insertion tool 14 when attaching the insertion tool 14 to a receiver 26 as will be described in greater detail below. The extension 216 has a substantially rectangular cross-section viewed in a plane perpendicular to the axis D. In particular, the extension includes a pair of substantially planar opposed sides 217, a pair of substantially curved opposed sides 218 and a curved top surface 219. The body 212 further includes an inner, curved entry aperture or easement 220 located opposite the extension 216 and an elongate hex-shaped aperture or driving socket 222 running along the axis D and communicating with the easement 220. The driving socket 222 is sized and shaped to receive and mate with the hex-shaped upper driving portion 204 of each of the lock pins 120. The socket 222 includes a stop or abutment surface 224, sized and shaped for frictional contact with the top surface 200 of the lock pin 120. Above the abutment surface 224 and extending through the upper extension 216, the illustrated lock pin driver 210 is substantially solid.

Figure 37:
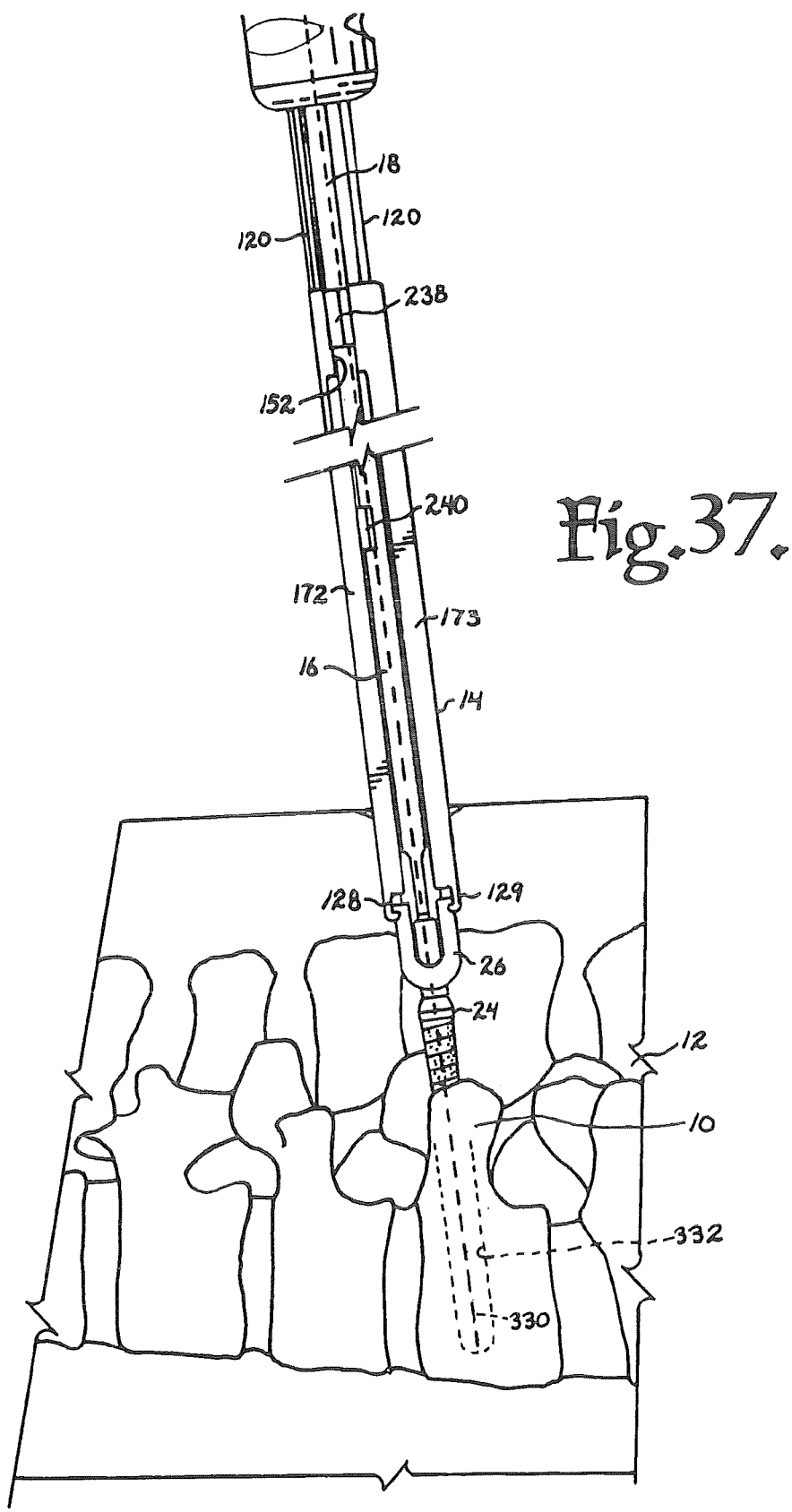
FIG. 37 is a partial and generally schematic view of a patient's spine showing a bone screw driver received within an insertion tool with an attached bone screw being guided toward a threaded bore in a vertebra in an early stage of a method according to the invention.

With reference to FIGS. 24-26, the bone screw driver 16 includes an upper elongate handle 230, an elongate shaft 232 and a driving end portion 234 integral with or fixedly attached to the shaft 232. The handle 230 is somewhat triangular when viewed on end as shown in FIG. 25. With reference to FIG. 24, the handle 230 includes shallow apertures 236 to aid a surgeon in gripping and rotating the handle 230. The handle 230 is fixed to and coaxial with the shaft 232 that has an axis of rotation E. Protruding laterally from the shaft 232 are an alignment tab 238 and a centering tab 240, the centering tab 240 being disposed between the alignment tab 238 and the driving end 234. With reference to the axis E, both of the tabs 238 and 240 extend radially outwardly from the shaft 232 as illustrated in FIGS. 24, 25 and 37. However, the tabs 238 and 240 are not substantially co-linear or co-planar. The two tabs 238 and 240 are sized, shaped and positioned to align with non-linear openings and/or surfaces in the insertion tool 14 to ensure proper engagement of the driver 16 driving end 234 within the U-shaped channel 76 of the bone screw receiver 26. Specifically, such proper engagement occurs when the alignment tab 238 is disposed in and extending through the channel 152 and the centering tab 240 is disposed in the through channel 148 below the surface 155 and abutting against the front face 172 as illustrated in FIG. 37 and will be described in greater detail below.

Near the driving end 234, the shaft 232 includes a lower portion 242 of reduced diameter. The driving end 234 further includes a curved lower surface 244 that smoothly transitions to opposed planar surfaces 245, the surfaces 244 and 245 being sized and shaped to be snugly received within the receiver U-shaped channel 76 and to fully engage inner surfaces of the arms 72 and 73 as well as the top curved surface 60 of the shank end portion 38. Opposed front and rear surfaces 246 of the driving end 234 are substantially planar and sized and shaped to be substantially flush with the receiver 26 along the sides 92 and 93, and extending from near the top surfaces 74 and 75 to the seating surface 78.

The driving tool 16 includes a longitudinal through bore 248 formed along an entire length thereof along the axis E. The through bore 248 cooperates with cannulated bone screws, allowing for insertion of the driver 16 and attached bone screw 1 over guide wires or pins.

Figure 28:
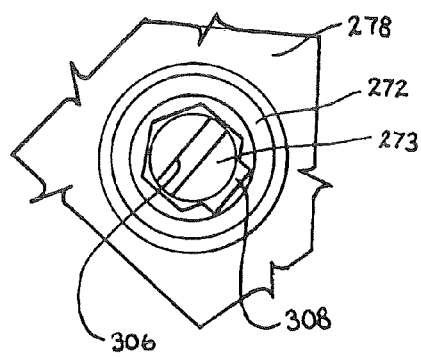
FIG. 28 is an enlarged and partial bottom plan view of the reduction tool of FIG. 27.

With reference to FIGS. 27-29, the reduction tool 18 is elongate, having an axis of rotation F and including a handle 260 that houses a driving tip extension and retraction mechanism, generally, 262, an upper shaft housing 264, a mid-shaft housing 266 having a threaded portion 268 and a lower shaft housing 270 attached to a driving tip housing 272 for an extendible driving tip 273. The handle, shaft housings and driving tip are all aligned along the axis of rotation F. The handle 260 further includes an upper end portion or palm handle 276 a lower grip portion 278 and a rotatable member or retraction lever 280 disposed between the upper 276 and lower 278 portions, the rotatable member or lever 280 being part of the extension and retraction mechanism 262.

With further reference to FIGS. 30-35, the lever 280 has a coarse inner thread 282 providing for a vertical travel distance to fully and accurately extend and retract the driving tip 273 in and out of the driving tip housing (in the illustrated embodiment, a vertical travel distance of about 3.5 mm) for a ¼ rotation of the lever 280. The mechanism 262 further includes an elongate shaft 285 attached to the driving tip 273 and extending along the axis F from the driving tip 273 to an upper screw 288 disposed substantially within the rotatable lever 280 when the driving tip 273 is in an extended, closure member engaging position as shown in FIGS. 27, 29, 30, 33 and 34. The screw 288 is fixed to the shaft 284 at one end thereof and fixed to a slidable member or stopper 290 at an opposite end thereof. The stopper 290 is disposed in a central void or aperture 292 formed in the upper handle portion 276. The screw 288 is sized and shaped to mate with the inner thread 282 of the rotatable lever 280 such that when the lever 280 is rotated a one quarter turn (ninety degrees) about the axis F in a clock-wise direction when viewed from the upper portion of the handle 276, the screw 288 is moved from the position shown in FIG. 30 linearly upwardly along the axis F to the position shown in FIG. 31. Such rotating action of the lever 280 also slides the stopper 290 upwardly in the aperture 292 to a position abutting against an upper wall or stop 296, with a portion of the screw 288 also disposed in the aperture 294 as illustrated in FIG. 31. The stop 296 prohibits any further upward movement of the screw 288, attached shaft 285 and attached driving tip 273, fully retracting the tip 273 into the housing 272. Likewise, when the driving tip 273 is in the fully extended position shown in FIGS. 27 and 30, the stopper 290 abuts against a lower wall or stop 298 that also defines the aperture 294, prohibiting any further downward movement of the driving tip 273.

A pair of pins 299 fix the upper handle portion 276 to the lower handle portion 278 and capture the rotatable lever 280 therebetween. As illustrated in FIG. 32, the lever 280 further includes inner curved channels 300, with the pins 299 received in and extending therethrough. The channels 300 are sized and shaped to allow the lever 280 to slidingly rotate the one quarter turn or ninety degrees required for extending and retracting the driving tip 273 as previously described herein, but prohibiting any additional rotation of the lever 280 in either direction.

Although not shown in the drawings, it is foreseen that the handle lower portion 278 may be imprinted or otherwise marked with the words "UP" and "DOWN" on a surface 302 thereof to reveal to the surgeon whether the driving tip 273 is extended or retracted. With respect to the illustrated embodiment, when the lever 280 is positioned over and covering the word "UP," the word "DOWN" would be uncovered and visible when the tool 18 is in the position shown in FIG. 30. After rotating one quarter turn as shown in FIG. 31, the lever 280 would be positioned over and covering the word "DOWN," leaving the word "UP" uncovered and visible to the surgeon. As illustrated in FIG. 34, the driving tip housing 272 provides adequate space about the driving tip 273 to allow for full retraction of the tip 273 into the housing 272. Specifically, the housing 272 forms a void or channel 304 sized and shaped to receive the driving tip 273 in the retracted position.

The driving tip 273 is substantially cylindrical and has a central through slot 306 and facets for capturing and holding the closure structure 28 prior to and during insertion in the receiver 26. The tip 273 further includes a lateral projection or key 308 sized and shaped to mate with the key slot 116 of the closure structure 28 for precise positioning of the closure structure 28 into the insertion tool 14 and the receiver 26 by the reduction tool 18. Specifically, the outer thread 268 formed on the reduction tool 18 is sized and shaped to rotatably mate with the thread 168 of the insertion tool 14. Furthermore a position of a leading surface 310 of the thread 268 and the leading surface 170 of the thread 168 are synchronized along with the positioning of the key 308 of the driving tip 273 so that a controlled, exact mating of the closure 28 with the receiver 26 is consistently accomplished. Finally, both the reduction tool 18 and the insertion tool 14 are sized and shaped such that the closure structure 28 is advanced till snug, but cannot be driven past the top surfaces 74 and 75 of the receiver 26, with a thread run-out portion 312 on the reduction tool 18 configured and positioned to stop rotation of the thread 268 with respect to the thread 168 of the insertion tool 14, prohibiting any further rotation or downward motion of the tool 18 with respect to the tool 14. The reduction tool 18, in cooperation with the insertion tool 14, provides apparatus for moving the cord 6 of the longitudinal connecting member 3 (or other type of connecting member, such as a coil or rod) downwardly in a controlled manner into the receiver 26 by rotating the reduction tool 18, and also thereby precisely mating the thread 268 with the guide and advancement structure 168, capturing the cord 6 or other longitudinal connecting member within the receiver 26.

Figure 36:
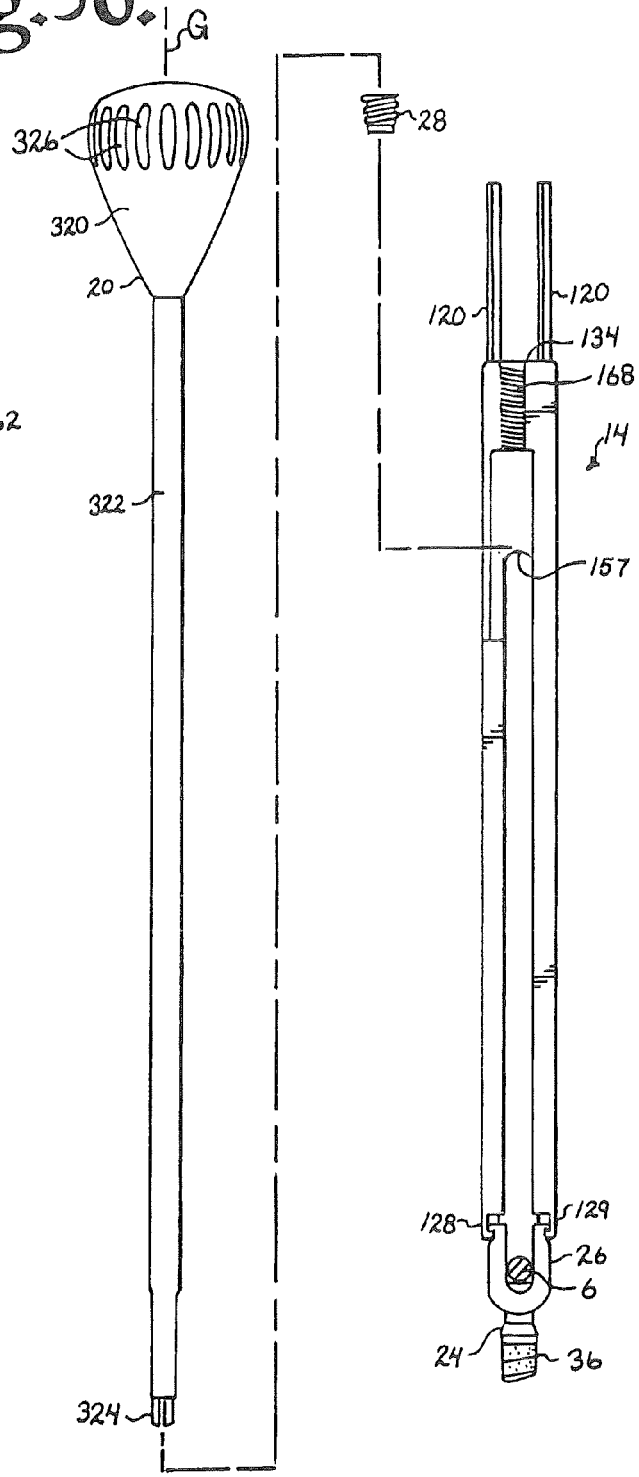
FIG. 36 is a partial and exploded front elevational view of a closure structure starter for use in accordance with the invention, further shown with a closure structure, a cord, and an insertion tool and attached bone screw.

With reference to FIG. 36, the closure starter 20 for use in methods of the invention includes a handle 320 fixed to an elongate cylindrical stem or shaft 322 and a driving tip 324 integral to the shaft 322. The handle 320, shaft 322 and tip 324 are coaxial along an axis of rotation G. The handle 320 includes shallow apertures 326 to aid a surgeon in gripping and rotating the starter 20 about the axis G when the starter 20 is engaged with a closure structure 28. The closure starter 20 is sized and shaped to be used in cooperation with the insertion tool 14, with the tip 324 in engagement with a closure structure 28 and the starter 20 extending through the tool 14 with the handle 320 located above the lock pins 120 to allow for adequate clearance between the handle 320 and the insertion tool 14 to allow for the rotation of the closure structure 28 into the receiver 26 by turning the handle 320. The driving tip 324 includes a slot and faceted geometry for capturing and holding the closure structure 28 prior to and during insertion of the structure 28 into the receiver 26. The closure starter 20 is useful when, as shown in FIG. 36, the cord 6 or other longitudinal connecting member has been previously reduced into the receiver 26 such that the reduction tool 18 is not required.

In use, the previously described tools are utilized to attach one or more longitudinal connecting member 3 to the human spinal column 12. The procedure is begun by selection of a bone screw 1 in accordance with the size of the patient's vertebra 10 and the requirements of the spinal support needed. The illustrated hinged bone screws 1 are preferred for use with the cord 6 and spacers 8 of the illustrated longitudinal connecting member 3. The hinged screw 1 advantageously allows for a plurality of angular or articulated locking positions between the shank 24 and the receiver 26. Also with respect to the cooperation between bone screws and the cord 6 and spacers 8 of the longitudinal connecting member 3, an advantage of both fixed screws and the hinged screw 1 over polyaxial bone screws is that the hinged or fixed screws maintain a set or constant distance between receivers that aids in keeping the cord 6 in a desired tension. Fixed bone screws as illustrated in FIGS. 40-49, an alternative hinged bone screw illustrated in FIGS. 52-54 and an alternative polyaxial bone screw illustrated in FIG. 55, are also described more fully below that may be utilized with tools according to the invention to attach one or more longitudinal connecting members 3 to a human spine 12. Furthermore, as will be described more fully below, other types of longitudinal connecting members may also be used according to the invention including rods and coils. Bone screws according to the invention are also preferably cannulated so as to be receivable over and guided by a guide pin or wire 330 as discussed more fully below.

With particular reference to FIGS. 1, 6 and 7, a hinged bone screw 1 of the invention may be assembled by up or bottom loading the bone screw shank 24 into the receiver 26 with the side surfaces 62 facing the inner side walls 107 of the receiver 26. The shank 24 is uploaded until the end portion 38 abuts against the upper wall surfaces 106. Thereafter, the shank 24 is rotated about the axis A about ninety degrees, followed by lowering the end portion 38 until the lowered curved surfaces 57 of the wing projections 56 contact the lower seat 78 of the receiver 26 at the locking teeth 80.

With particular reference to FIGS. 10-23, the insertion tool 14 may be placed into engagement with the hinged bone screw 1 as follows: The bone screw receiver 26 that has been attached to a shank 24 as previously described herein is first aligned with an insertion tool 14 by aligning the laser etched stripe 98 of the receiver with the laser etched stripe 100 of the insertion tool 14. Such alignment places the side 144 of the insertion tool 14 and the side 72 of the receiver 26 facing in the same direction and the through channel 148 communicating and aligned with the U-shaped channel 76 of the receive 26. The upper extension 216 of the lock pin driver 210 may then be inserted into the channel 148 with the opposed planar sides 217 being received in the channel 148. The lock pin driver 210 is then rotated about its axis D causing the opposed curved sides 218 to abut against the surfaces forming the channel 148 to spread the tangs 128 and 129 apart, followed by inserting the tool 14 onto the bone screw receiver 26 outer arm surfaces 72 and 73 at a location spaced from the top surfaces 74 and 75. The lock pin driver 210 is rotated again, thereby releasing the tool 14 from the curved surfaces 218 and thus snapping the tool 14 onto the receiver 26. Thereafter the lock pin extension 216 is removed from the through channel 148 and the insertion tool 14 is pulled upwardly and away from the receiver 26, the tool 14 sliding upwardly along the inwardly sloping surfaces 88 and 89 leading up to the undercut grooves 86 and 87 until the projections 186 and 187 are received and engaged with the receiver 26 at the respective grooves 86 and 87. Such engagement results in a firm attachment that also resists any attempt to spread or splay the tangs 128 and 129. Also, the raised strip 194 of the tool 14 is received in the slit 94 of the receiver and the raised strip 195 of the tool 14 is received in the slit 95 of the receiver. The raised strips 194 and 195 also extend upwardly from the top surfaces 74 and 75 of the receiver 26 as illustrated in FIG. 23.

With particular reference to FIGS. 19 and 23, a pair of lock pins may then be inserted in the insertion tool 14 cylindrical channels 158 and 162 with each lock pin tip or bottom 202 being inserted into the channels at the top surface 134 and guided downwardly toward the bottom 136 of the tool 14. Once the threaded portion 206 makes contact with the threaded inner wall 160 or 164, the lock pin 120 is rotated and driven downwardly toward the receiver surface 74 or 75 by mounting the lock pin driver 210 on a lock pin 120 with the driving portion 204 of the pin 120 received in the elongate socket 222 and the top 200 of the pin 120 abutting against and frictionally engaging the top surface or stop 224. The lock pin driver 210 is rotated about the axis D until the bottom surface 202 frictionally engages with the receiver surfaces 74 or 75. With respect to the pin 120 abutting the surface 74, the raised strip 194 prohibits movement of the pin 120 toward the receiver side surface 92. With respect to the pin 120 abutting the surface 75, the raised strip 195 prohibits movement of the pin 120 toward the opposite receiver side surface 93. Thus the two strips 194 and 195 cooperate to prevent front to back movement of the insertion tool 14 between the receiver side surfaces 92 and 93.

With reference to FIGS. 24-26 and 37, after installation of the insertion tool 14 on the bone screw receiver 26, the driver 16 is inserted into the insertion tool 14 by inserting the driving end 234 into the lateral opening 149 of the longitudinal channel 132 near the top 134 of the tool 14 with the shaft 232 being received in the narrow channel 152, followed by sliding the shaft 232 downwardly along the axis C into the interior of the tool 14 with both the alignment tab 238 and the centering tab 240 aligned with and then passing into the narrow channel 152 at the front 140 of the alignment tool 14. By aligning the tabs 238 and 240 with the front 140 of the tool 14, the driving end 234 of the driver 16 is set up for proper engagement with the receiver 26 and the end portion 38 of the shank 24. The tab 240 is then passed through the narrow channel 152 and into the through channel 148. Once the tab 238 enters the channel 152 and is fully received thereby, the driving end lower surface 244 engages the top surface 60 of the end portion 38 of the shank 24 and the lower seat 78 of the receiver 26. The driving end 234 also contacts the receiver 26 along an entire height of the U-shaped channel 76 from the lower seat 78 to the upper surfaces 74 and 75. The driver 16 is now in position to drive the bone screw 1 into a vertebra 10 as illustrated in FIG. 37. The alignment tab 238 cooperating with and engaging the surfaces forming the channel opening 152 and the centering tab 240 cooperating with and engaging the front face 172 of the tool 14 keep the driving end 234 in proper position, fully engaging the receiver 26 as the driver 16 is manually rotated about the axis E to rotate and drive the bone screw 1 into the vertebra 10 as will be described more fully below. Thereafter, the driver 16 may be removed by simply sliding the shaft 232 upwardly along the axis C and then laterally out of the tool 14 through the upper side opening formed by the channel 152, with the driving end 234 being easily removable out of the squared off opening 149 of the upper portion of the channel 148.

With particular reference to FIGS. 37-39, a relatively minimally invasive incision or incisions are made and stretched so as to snugly receive the tools of the invention. A drill (not shown) is utilized to form a first guide bore in a vertebra 10 under guidance of non invasive imaging techniques, which procedure is well known and established. A thin pin or guide wire 330 is then inserted in the first guide bore, the pin and guide bore functioning to minimize stress on the vertebra 10 and providing an eventual guide for the placement and angle of the bone screw shank 24 with respect to the vertebra 10. Then the guide bore is enlarged utilizing a cannulated drilling tool or tap having an integral or otherwise attached cannulated and threaded bit with an outer surface sized and shaped to correspond to the size and shape of the chosen threaded bone screw 1.

With the pin 330 fixed to the vertebra 10 and in place in an enlarged guide bore 332 and extending upwardly through the bore and out of the incision, the pin 330 is threaded into the bore 66 at the tip 44 of the shank 24 and out of the opening at the top surface 66 of the bone screw shank 24. The pin 330 is then threaded into the driver 16 at the bore 248 opening at the surface 244 and then up through the bore 248 of the driver 16. Care is taken to insure that the axis A of the bone screw shank 24 is aligned and coaxial with the axis B of the receiver when the driver 16 driving end 234 engages the top surface 60 of the bone screw shank 24. Thereafter, driver contact with the surface 60 of the shank 24 maintains coaxial alignment of the shank and receiver during driving of the shank body 36 into the vertebra 10. With the driver 16 installed on the insertion tool 14 properly aligned as illustrated in FIG. 37 and as previously described herein, the bone screw 1 is then rotated and driven into the tapped bore 332 in the vertebra 10 with the surgeon holding and rotating the bone screw assembly 1 and the insertion tool 14 with the driver handle 230 until the shank body 36 is disposed at a desired depth in the tapped bore 332 of the respective vertebra 10.

With reference to FIG. 39, at least two and up to a plurality of bone screws 1 with attached insertion tools 14 are installed in each vertebra 10 to be attached to the longitudinal connecting member 3. After a specific bone screw 1 is installed, the driver 16 is removed by sliding the shaft 232 up through the open top 134 of the tool 14, out of the side opening and away from the bone screw 1 and the attached insertion tool 14.

With reference to FIGS. 38 and 39, the reduction tool 18 is then used to press the longitudinal connecting member 3 or other type of longitudinal connecting member, such as a rod or coil, downwardly into the receivers 26 of the implanted bone screws 1. In the embodiment shown, a spacer 8 is cut to length and pre-loaded onto a cord 6 then the cord 6 of the longitudinal connecting member 3 is inserted into and through a through bore 148 of an insertion tool 14 with a tail or end 334 of the cord 6 extending out of the bore 148. The other end of the cord 6 is then inserted into a through bore 148 of an adjacent insertion tool 14, followed by the threading of another spacer 8, with such process continuing until a threaded spacer 8 of appropriate length is disposed between each of the insertion tools 14 with the cord extending through each through bore 148, either above or below the patient's skin. Then all of the spacers 8 are pressed downwardly through the incision and generally between the insertion tools 14 and near the bone screw receivers 26.

Prior to engagement with an insertion tool 14, the reduction tool 18 is attached to a closure structure 28 as follows: The reduction tool 18 driving tip 273 is placed in an extended, closure structure engaging position as shown in FIG. 27 by rotating the lever 280 one quarter turn in a clock-wise direction, if necessary, to fully expose the tip 273. The closure structure 28 is then placed on the driving tip 273 with the tip 273 fully engaging the internal drive socket 115 and the laterally projecting key 308 being received in the key slot 116, the driving tip 273 surfaces and key 308 frictionally holding the closure structure 28 on the driving tip 273 as the structure 28 is inserted into the open longitudinal channel 132 through the side opening 149 near the upper end or top 134 of the tool 14, the reduction tool lower shaft housing 270 being received in the narrow channel 152. The closure structure 28 and attached reduction tool housing portions 266, 270 and 272 are then slidingly received and lowered in the longitudinal channel 132 along the axis C until the threaded portion 268 of the tool 18 makes contact with the guide and advancement structure 168 disposed near the top of the insertion tool 14.

With particular reference to FIG. 38, the reduction tool 18 is then rotated about the axes C and F by rotating the handle 260 to move the closure structure 28 toward the receiver 26 in a controlled manner. During such rotation, the closure structure bottom surface 113 makes contact with the cord 6 and presses the cord 6 downwardly and toward and into the channel 76 of the receiver 26. As previously stated herein, the starting locations 170 and 310 of the respective mating guide and advancement structures 168 and 268, as well as the key 308 on the driving tip 273 and the key slot 116 on the closure structure 28 are all positioned to precisely mate the closure structure guide and advancement structure 110 with the receiver guide and advancement structure 82. Furthermore the guide and advancement structures 168 and 268 are sized and positioned such that once the closure structure 28 is threaded fully into the receiver 26 with the top surface 112 of the closure structure 28 being flush with the top surfaces 74 and 75 of the receiver 26, further rotation of the tool 18 may be prohibited by abutment of the guide and advancement structure 168 with an optional thread run out stop 312 on the reduction tool 18. At such time, the cord 6 is captured in the receiver 26 and the closure structure 28 may or may not be fully tightened and torqued within the receiver 26.

The driving tip 273 of the reduction tool 18 is then retracted by rotating the lever 280 of the handle 260 in a counter-clockwise direction one quarter turn, detaching the driving tip 273 from the closure structure 28, thereby deploying it. The reduction tool 18 may then be removed from the insertion tool 14 by rotating the handle 260 in a counter-clockwise direction to move the tool 18 upwardly and away from the receiver 26. Once the guide and advancement structure 268 is disengaged from the guide and advancement structure 168, the tool 18 may be pulled up and slid sideways out of the tool 14.

With reference to FIG. 39, in order to install a longitudinal connecting member 3 in two or more bone screws 4, it may or may not be necessary to equip each insertion tool 14 with a reduction tool 18. It may be sufficient to utilized the reduction tool 18 with only one insertion tool 14, for example the bone screw receiver 26 and attached insertion guide tool 14 shown in both FIGS. 38 and 39 located at an end of a group of bone screws, shown having a tail 334 of the cord 6 extending therefrom. Thereafter, the closure structures 28 may be placed in the remaining receivers 26 utilizing the closure starter 20.

The closure starter 20 may be used similarly to the reduction tool 18, with the closure structure 28 first placed on the tool 20 with the driving tip 324 engaging the internal drive socket 115, the driving tip 324 surfaces and slot holding the closure structure 28 on the driving tip 324 as the structure 28 is side-loaded into the longitudinal channel 132 of the tool 14 with the driving tip 324 and attached structure 28 inserted into the lateral opening 149 of the tool 14 and a lower portion of the shaft 322 being received in the narrow channel 152 formed near the top of the tool 14. The closure structure 28 and attached closure starter shaft 322 are then slidingly received in the channel 132 along the axis C until the guide and advancement structure 110 of the closure structure 28 makes contact with the guide and advancement structure 82 of the receiver 26. The closure starter 20 is then rotated about the axis G by rotating the handle 320 to rotate and drive the closure structure 28 into the receiver 26. During such rotation, the closure structure bottom surface 113 contacts the cord 6 and presses the cord 6 into the channel 76 of the receiver 26. At such time, the cord 6 is captured in the receiver 26. The closure structure 28 may or may not be fully tightened and torqued within the receiver 26. For removal, the closure starter 20 is simply moved upwardly and away from the receiver 26 and then out of the insertion tool 14.

Once all of the closure structures 28 are in a seated position in respective bone screws 1 and the surgeon is satisfied with the position of all of the elements, the structures 28 may be locked into place with an elongate driving or torquing tool having a driving tip similar or identical to the reduction tool 18 driving tip 273 or the closure starter 20 driving tip 324 as well as an elongate shaft sized and shaped to be slidingly received in the insertion tool 14. Such a torquing tool typically includes a T-shaped handle to aid the surgeon in applying adequate tightening force, typically 70-120 inch pounds, to fully tighten and set the closure structure 28 within the receiver 26 so that the surface 113 is snug against the cord 6. An anti-torque holding tool may be utilized to hold the insertion tool 14 during tightening with the torquing tool. Such an anti-torque holding tool is also elongate and includes a hollow shaft sized and shaped to slidingly mate over the insertion tool 14. Therefore, such an anti-torque holding tool would be substantially rectangular in cross-section, sized and shaped to closely fit about the insertion tool 14, and include a handle for holding the insertion tool 14 in place during rotation of the torquing tool, thereby allowing a surgeon to counter the torque applied by the insertion tool 14 when applying torque to the closure structure 28. The antitorque tool typically also has an upper handle with an opening through which the torquing tool passes. Although designed for use with a cylindrical insertion tool, the torquing tool and anti-torque tool combination illustrated in U.S. patent application Ser. No. 10/789,149, filed Feb. 27, 2004 may be instructive here, the disclosure of which is incorporated by reference herein. Furthermore, a cord tensioning instrument as is known in the art is used to place tension on the cord 6 as each closure structure 28 is torqued and tightened.

After all of the closure structures 28 have been locked into place and the cord 6 adequately tightened, each of the insertion tools 14 are removed by mounting the lock pin driver 210 onto each lock pin 120 and loosening each of the pair of pins 120 from the insertion tool 14 by rotating the driver 210 in a counter-clockwise direction. Each pin 120 is then rotated upwardly and away from the tool 14. Downward force is then placed on the insertion tool 14 by the surgeon to move the implant engaging members or projections 186 and 187 out of the grooves 86 and 87 of the receiver 26. Then the lock pin driver upper extension 216 is inserted into the channel 148 with the opposed planar sides 217 being received in the channel 148. The lock pin driver 210 is then rotated about its axis D causing the opposed curved sides 218 to abut against the surfaces forming the channel 148 to spread the tangs 128 and 129 apart, followed by removing the tool 14 from the bone screw receiver 26 outer arm surfaces 72 and 73 and axially upwardly away from the receiver 26. The lock pin driver 210 is rotated again, thereby releasing the tool 14 from the curved surfaces 218. Thereafter the lock pin extension 216 is removed from the through channel 148 and the insertion tool 14 is pulled away from the bone screw 1 and out of the incision 350. Such procedure is followed to remove each insertion tool 14 out of the incision.

With reference to FIGS. 40-42 an alternative open fixed bone screw generally 340 according to the invention and for use with the tools 14, 16, 18 and 20 of the invention includes a receiver 342 fixed to a shank 344. The bone screw 340 is substantially similar to the bone screw 1 with the exception that the fixed shank 344 cannot be articulated with respect to the receiver 342 and is thus in fixed substantially coaxial relationship therewith.

Similar to the shank body 36 of the bone screw 1, the shank 344 of the bone screw 340 is elongate, having a helically wound, radially outwardly extending bone implantable thread 346 axially extending from near a lower end or tip 348 of the body 346 to near the receiver 342. To provide a biologically active interface with the bone, the threaded shank 344 is coated, perforated, made porous or otherwise treated 350. The treatment 350 may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding. In the illustrated embodiment, the shank 344 is cannulated with a small central bore 352 extending an entire length of the shank. The bore 352 is coaxial with the threaded body 344 and opens at the tip 348 and also at a curved seating surface 354, providing a passage through the shank interior for a length of wire or pin inserted into the vertebra 10 prior to the insertion of the shank 344, the wire or pin providing a guide for insertion of the shank body 344 into the vertebra 10.

The receiver 342 includes a base 356 integral with a pair of opposed upstanding arms 358 and 359 that extend from the base 356 to respective top surfaces 360 and 361. The arms 358 and 359 form a U-shaped cradle and define a U-shaped channel 364 between the arms 358 and 359 and include an upper opening 365 and the lower seating surface 354. The lower seating surface 354 is sized and shaped to engage the cord 6 of the longitudinal connecting member 3 previously described herein. Each of the arms 358 and 359 has an interior surface that defines an inner cylindrical profile and includes a discontinuous helically wound guide and advancement structure 366. In the illustrated embodiment, the guide and advancement structure 366 is a partial or discontinuous helically wound flangeform configured to mate under rotation with the guide and advancement structure 110 on the closure structure 28, as similarly previously described herein with respect to the bone screw 1. However, it is foreseen that the guide and advancement structure 366 could alternatively be a buttress thread, a square thread, a reverse angle thread or other thread like or non-thread like helically wound advancement structure for operably guiding under rotation and advancing the closure structure 28 downward between the arms 358 and 359 and having such a nature as to resist splaying of the arms 358 and 359 when the closure 28 is advanced into the U-shaped channel 364.

Each of the arms 358 and 359 has a substantially planar outer surface 370 and 372, respectively, that includes a substantially linear undercut tool engagement groove 374 and 375, identical to the tool engagement grooves 86 and 87 described previously herein with respect to the bone screw 1 that are sized and shaped to engage the insertion tool 14 projections 186 and 187. Further, offset opposed insertion tool engaging slits 378 and 379 are identical to the slits 94 and 95 described previously herein with respect to the bone screw 1. The side 370 further includes a laser etched stripe 380 for alignment with the similar stripe 100 on the tool 14, also as previously described herein with respect to the bone screw 1. Opposed front and back surfaces 382 and 383, respectively, are both substantially planar and parallel.

Figure 50:
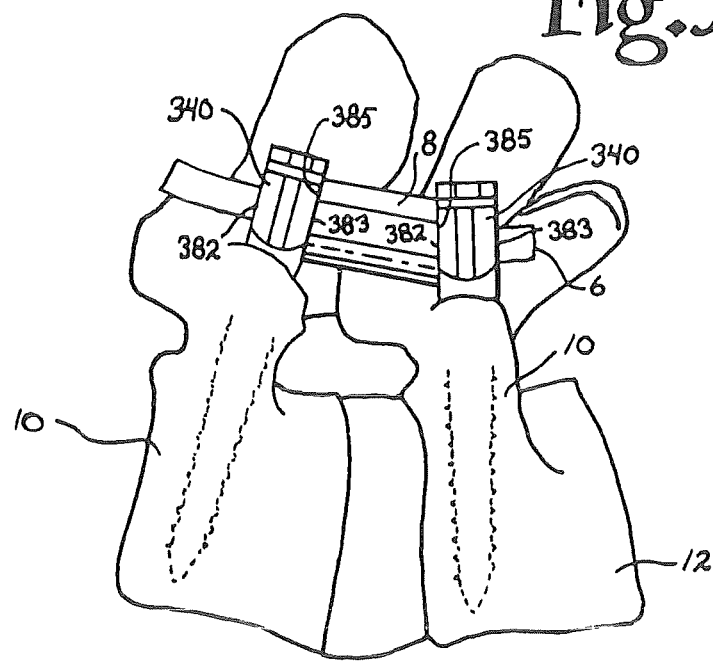
FIG. 50 is a partial and generally schematic view of a patient's spine, showing two implanted monoaxial bone screws according to FIGS. 40-42 with a connecting cord and spacer having non-parallel end surfaces.

As illustrated in FIG. 50, when two bone screws 340 of the invention are utilized that have planar parallel front and back surfaces 382 and 383, the opposed sides 9 of the spacer 8 may need to be cut or otherwise sized to be non-parallel in order to create or preserve spinal lordosis or kyphosis. In the embodiment illustrated in FIG. 50 the spacer 8 has substantially trapezoidal opposing sides 385 to create or preserve spinal lordosis at one or more motion segments.

The bone screw 340 cooperates with the insertion tool 14 and the reduction tool 18 in a manner identical to the cooperation between the bone screw 1 and such tools as previously described herein. With respect to the bone screw driver 16, the receiver portion forming the U-shaped channel 364 and the lower seat 354 cooperate with the driver 16 in a manner similar to the cooperation between the receiver 26 portion forming the U-shaped channel 76 and the lower seat 78 and upper surface 60 of the hinged shank 24.

With reference to FIGS. 43-46, additional alternative open fixed screws according to the invention are illustrated that include receivers having opposed surfaces for creating or preserving spinal lordosis or kyphosis. Rather than modifying the spacer 8 as illustrated in FIG. 50, such bone screws allow for the use of a standard or consistent spacer 8 with parallel sides surfaces 9, with the bone screw receiver being shaped to compensate for or create spinal lordosis or kyphosis at one or more motion segments.

FIGS. 43 and 44 illustrate open fixed bone screws 387 and 388, respectively, having respective "lordosing" receiver opposed surfaces 390 and 391. And FIGS. 45 and 46 illustrate open fixed bone screws 393 and 394 respectively, having respective "kyphosing" receiver opposed surfaces 396 and 397. With the exception of the opposed side surfaces 390, 391, 396 or 397, the respective bone screws 387, 388, 393 and 394 are substantially identical to the bone screw 340 previously described herein and such discussion is incorporated by reference with respect to the screws 387, 388, 393 and 394. Therefore the bone screws 387, 388, 393 and 394 all fully cooperate with each of the tools 14, 16, 18 and 20 as previously described herein with respect to the bone screw 340 and also the bone screw 1.

Figure 51:
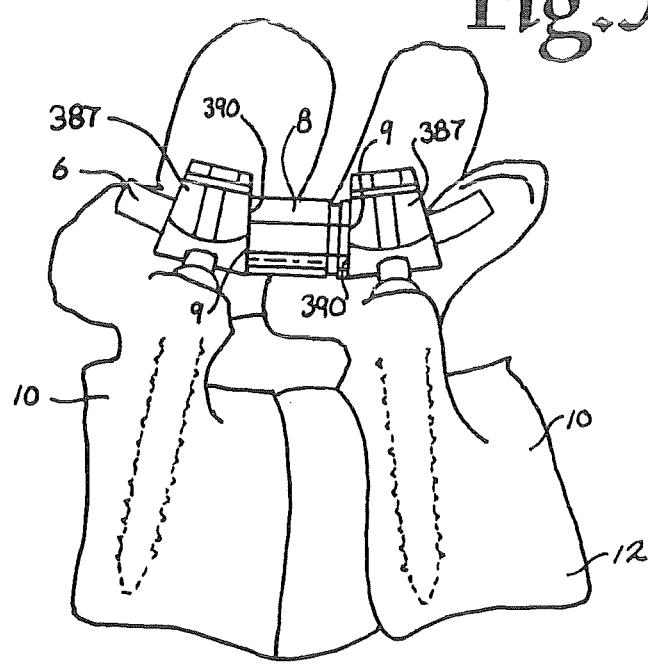
FIG. 51 is a partial and generally schematic view of a patient's spine, showing two implanted bone screws according to FIG. 43 with a connecting cord and spacer.

With respect to the bone screws 387 and 388 illustrated in FIGS. 43, 44 and 51, the "lordosing" pair of opposed surfaces 390 and pair of opposed surfaces 391 each define receivers with lateral trapezoidal profiles, that are wider at the bottom than at the top of the receiver, so that when a pair of such bone screw receivers are compressed against opposed parallel sides 9 of a spacer 8, the bone screw shanks will diverge, thereby creating or preserving lordosis, as illustrated in FIG. 51. As can be seen in the drawings, the bone screws 390 and 391 differ from one another only in the angle or degree of upward convergence of the sides 390 or the sides 391, corresponding to a degree of segmental lordosis occurring or desired in a patient's spine. For example, the bone screw 387 corresponds to about ten degrees lordosis while the bone screw 388 corresponds to about five degrees lordosis. It is foreseen that other bone screws according to the invention may be made that result in greater or lesser degrees of lordosis. Furthermore, it is noted that, for example, three or more bone screws 387 may be implanted in adjacent vertebrae resulting in a greater regional lordosis, for example, of forty degrees or more.

With respect to the bone screws 393 and 394 illustrated in FIGS. 45 and 46, the "kyphosing" pair of opposed surfaces 396 and pair of opposed surfaces 397 each define receivers with inverted lateral trapezoidal profiles, that are wider at the top than at the bottom of the receiver, so that when a pair of such bone screw receivers are compressed against opposed parallel sides 9 of a spacer 8, the bone screw shanks will converge, thereby creating or preserving segmental or regional kyphosis. As can be seen in the drawings, the bone screws 393 and 394 differ from one another only in the angle or degree of upward divergence of the sides 393 or the sides 394, corresponding to a degree of kyphosis occurring or desired in a patient's spine. For example, the bone screw 393 corresponds to about five degrees kyphosis while the bone screw 394 corresponds to about ten degrees kyphosis. It is foreseen that other bone screws according to the invention may be made that result in greater or lesser degrees of kyphosis. Also, it is foreseen that up to a plurality of kyphosing screws 393 and 394 may be used to create or preserve a greater amount of regional kyphosis.

Figure 47:
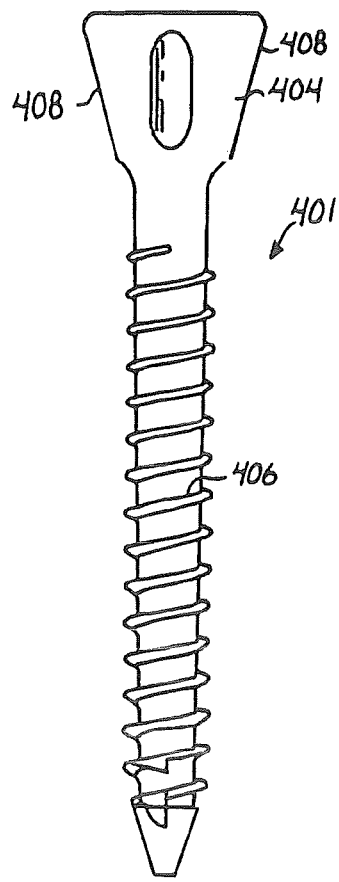
FIG. 47 is a side elevational view of a sixth alternative monoaxial bone screw according to the invention having a closed receiver and reverse trapezoidal profile.
Figure 48:
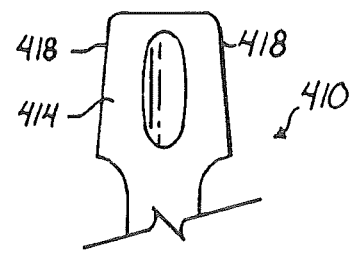
FIG. 48 is a partial side elevational view of a seventh alternative monoaxial bone screw according to the invention having a closed receiver and trapezoidal profile.
Figure 49:
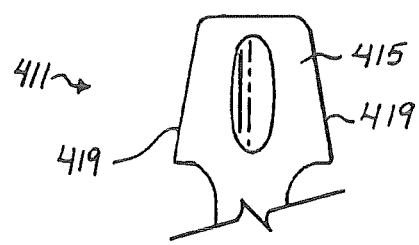
FIG. 49 is a partial side elevational view of an eighth alternative monoaxial bone screw according to the invention having a closed receiver and trapezoidal profile.

With reference to FIGS. 47-49, alternative lordosing and kyphosing closed bone screws according to the invention are illustrated. With reference to FIG. 47, a kyphosing closed bone screw, generally 401, includes a receiver 404 having a closed inner channel for receiving a cord 6 of a longitudinal connecting member 3 therethrough. The receiver 404 is fixed to a threaded shank 406 for implantation into a vertebra 10. The receiver 404 includes opposed upwardly diverging surfaces 408 defining an inverted lateral trapezoidal profile that is wider at the top than at the bottom of the receiver 404, so that when the receiver 494 is compressed against parallel sides 9 of a spacer 8, adjacent bone screw shanks 406 will converge, thereby creating or preserving kyphosis. The receiver 404 corresponds to about ten degrees kyphosis. It is foreseen that other closed bone screws according to the invention may be made that result in greater or lesser degrees of kyphosis. Also, it is foreseen that up to a plurality of kyphosing screws 401 may be used to create or preserve a greater amount of regional kyphosis.

With reference to FIGS. 48 and 49, closed lordosing screws generally 410 and 411, respectively, are illustrated. Both of the screws 410 and 411 have respective receivers 414 and 415, that are each fixed to a bone screw shank similar or identical to the shank 406. Each receiver 414 and 415 has a closed inner channel for receiving a cord 6 of a longitudinal connecting member 3 therethrough. The receivers 414 and 415 have respective "lordosing" opposed surfaces 418 and opposed surfaces 419, that define lateral trapezoidal profiles, that are wider at the bottom than at the top of the receiver, so that when a pair of such bone screw receivers are compressed against opposed parallel sides 9 of a spacer 8, the bone screw shanks will diverge, thereby creating or preserving lordosis. As can be seen in the drawings, the bone screws 410 and 411 differ from one another only in the angle or degree of upward convergence of the sides 418 or the sides 419, corresponding to a degree of lordosis occurring or desired in a patient's spine. For example, the bone screw 418 corresponds to about five degrees lordosis while the bone screw 419 corresponds to about ten degrees lordosis. It is foreseen that other bone screws according to the invention may be made that result in greater or lesser degrees of lordosis. Furthermore, it is noted that, for example, three or more bone screws 411 may be implanted in adjacent vertebrae resulting in a greater regional lordosis, for example, of forty degrees or more.

Figure 52:
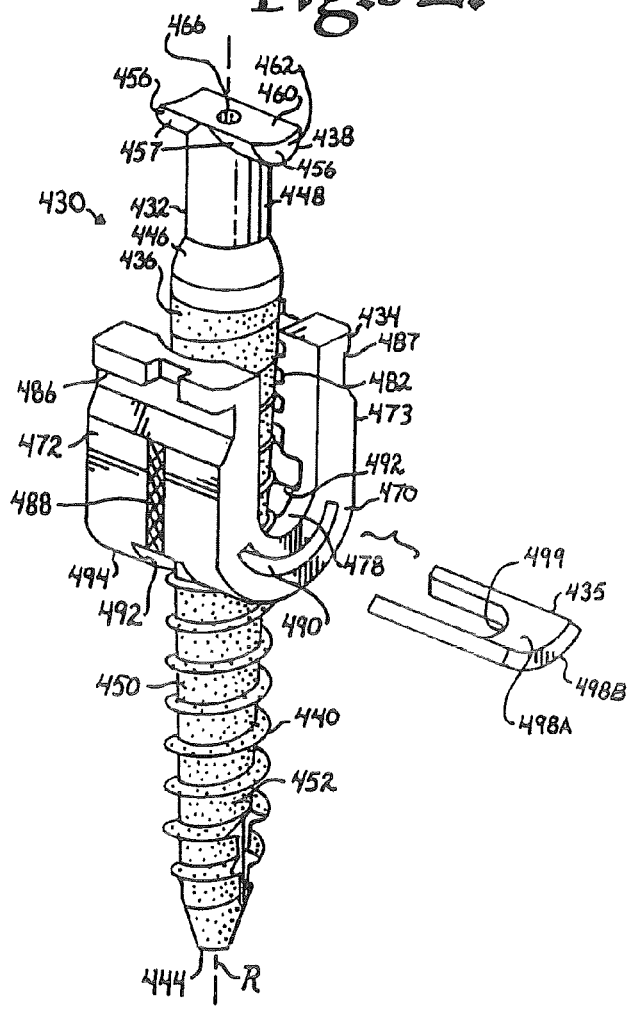
FIG. 52 is a perspective and partially exploded view of an alternative hinged screw according to the invention including a shank, a receiver and an attachment clip.
Figure 53:
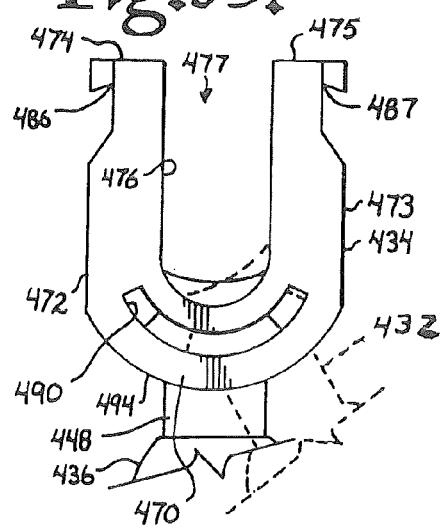
FIG. 53 is an enlarged and partial front elevational view of the hinged screw of FIG. 52 and shown in a second position in phantom.
Figure 54:
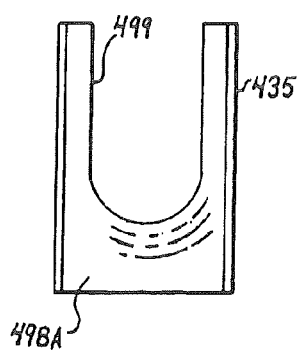
FIG. 54 is an enlarged top plan view of the attachment clip of FIG. 51.
Figure 55:
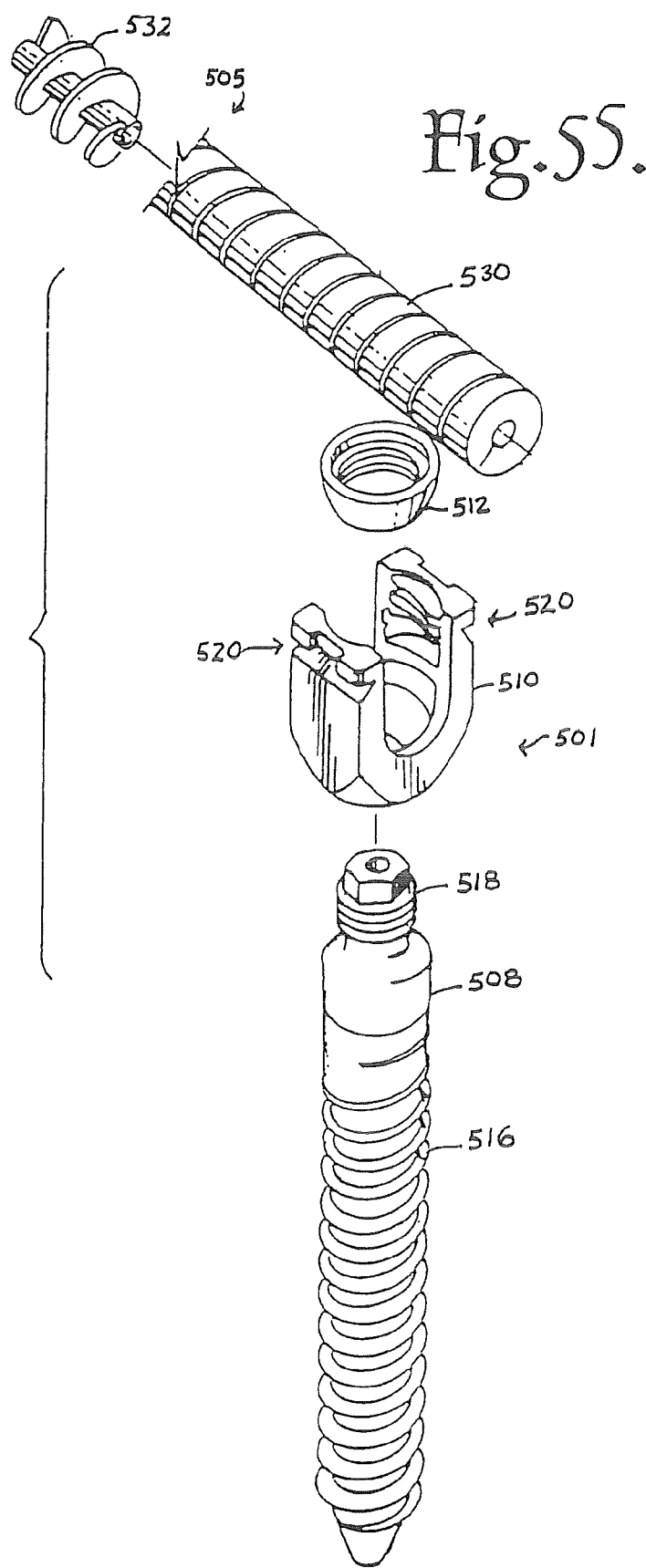
FIG. 55 is an enlarged and exploded perspective view of a polyaxial bone screw assembly according to the invention shown with a dynamic longitudinal connecting member for use according to the invention.

With reference to FIGS. 52-54, the reference numeral 430 generally designates an alternative hinged bone screw assembly according to the invention for cooperation with the dynamic stabilization connecting member 3 or other longitudinal connecting members including, but not limited to solid and hollow rods and coil-like members. Similar to what has been described previously herein with respect to the hinged bone screw 1, the hinged bone screw 430 also cooperates with the closure structure 28 and may be manipulated by using the insertion tool 14, the bone screw driver 16, the reduction tool 18 and the closure starter 20.

The hinged bone screw assembly 430 includes a shank 432, a receiver 434 and an insert 435 for attaching the shank 432 to the receiver 434. The shank 432 is substantially similar to the shank 24 of the assembly 1. Specifically, the shank 432 includes a body 436 integral with an upwardly extending end portion 438. The shank 432 and the receiver 434 are assembled using the insert 435 prior to implantation of the shank body 436 into the vertebra 10. The shank 432 of the bone screw assembly 430, is elongate, having an axis of rotation R. The shank body 436 has a helically wound, radially outwardly extending bone implantable thread 440 axially extending from near a lower end or tip 444 of the body 436 to near a slanted or sloped surface 446 that is adjacent to a smooth substantially cylindrical surface 448 located adjacent to the end portion 438. During use, the body 436 utilizing the thread 440 for gripping and advancement is implanted into the vertebra 10 leading with the tip 444 and driven down into the vertebra 10 with the driving tool 16 so as to be implanted in the vertebra 10 to near the sloped surface 446.

To provide a biologically active interface with the bone, an outer surface 450 of the shank body 36 that includes the thread 440 and extends between the surface 446 and the tip 444 is coated, perforated, made porous or otherwise treated 452. The treatment 452 may include, but is not limited to a plasma spray coating or other type of coating of a metal or, for example, a calcium phosphate; or a roughening, perforation or indentation in the surface 450, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$).

The sloped surface 446 extends radially inward and axially upward from the shank body 436 to the cylindrical portion 448. Further extending laterally outwardly from the cylindrical portion 448 is the upper end portion 438 that provides a connective or capture apparatus disposed at a distance from the threaded shank body 436 and thus at a distance from the vertebra 10 when the body 436 is implanted in the vertebra 10. The upper end portion 438 is configured for connecting the shank 432 to the receiver 434 and capturing the shank 432 in the receiver 434. The upper end portion 438 has a pair of projections or wings 456 that extend laterally oppositely outwardly from the cylindrical surface 448. Each projection 456 has a lower curved, convex surface 457 shaped to engage a concave seating surface of the receiver 434, to be described more fully below. The shank 432 is sized and shaped for top- or down-loading of the shank 432 into the receiver 434 as illustrated in FIG. 52, with the insert 435 thereafter being received in the receiver 434 and engaging the shank 432 at the cylindrical surface 448 and prohibiting upward motion of the shank 432 out of the channel opening 477. The upper or end portion 438 further includes a top surface 460 that includes a concave portion sized and shaped for receiving and engaging the driver 16 and also the cord 6. A side surface 462 extends between the top surface 460 and each curved lower surface 457.

In the illustrated embodiment, the shank 432 is cannulated with a small central bore 466 extending an entire length of the shank along the axis R. The bore 466 is coaxial with the threaded body 436 and opens at the tip 444 and the top surface 460, providing a passage through the shank interior for a length of wire or pin inserted into the vertebra 10 prior to the insertion of the shank body 436, the wire or pin providing a guide for insertion of the shank body 436 into the vertebra 10.

The receiver 434 is substantially similar to the receiver 26 of the assembly 1, including a base 470 integral with a pair of opposed upstanding arms 472 and 473 that extend from the base 470 to respective top surfaces 474 and 475. The arms 472 and 473 form a U-shaped cradle and define a U-shaped channel 476 between the arms 472 and 473 and include an upper opening 477 and a lower seat 478. The lower seat 478 is sized and shaped to cooperate with and frictionally engage the lower surfaces 457 of the shank upper end portion 438. Each of the arms 472 and 473 has an interior surface that defines an inner cylindrical profile and includes a discontinuous helically wound guide and advancement structure 482. In the illustrated embodiment, the guide and advancement structure 482 is a partial or discontinuous helically wound flangeform configured to mate under rotation with a similar structure on the substantially cylindrical closure structure 28 as previously discussed herein with respect to the receive 26. However, it is foreseen that the guide and advancement structure 482 could alternatively be a buttress thread, a square thread, a reverse angle thread or other thread like or non-thread like helically wound advancement structures for operably guiding under rotation and advancing a closure structure downward between the arms 472 and 473 and having such a nature as to resist splaying of the arms 472 and 473 when the closure 28 is advanced into the U-shaped channel 476.

Each of the arms 472 and 473 has planar outer surfaces, ledges, slits and linear undercut tool engagement grooves 486 and 487 identical to the outer arm surfaces, ledges, slits and grooves 86 and 87, respectively, previously described herein with respect to the bone screw receiver 26. Such grooves and surfaces allow for easy, sliding engagement and release of the tool 14 from the bone screw receiver 434, identical to what has been previously described herein with respect to the bone screw assembly 1. The receiver arm 472 outer side surface further includes a centrally located laser or otherwise etched alignment stripe 488 running from near the groove 486 to near the receiver base 470. The stripe 488 is similar to the stripe 98 on the bone screw receiver 26 previously described herein and cooperates with the similar stripe 100 on the insertion tool 14 (illustrated in FIGS. 38 and 39), providing a visual aid and ease in the alignment and proper attachment of the insertion tool 14 with the receiver 434 by linearly aligning the stripe 488 with the stripe 100. The receiver 434 base 470 also has a laterally opening curved channel or slot 490 sized and shaped to slidingly receive the insert 435. The lateral slot 490 communicates with the U-shaped channel 476 and also with a bottom curved slot 492 that also communicates with the U-shaped channel 476 and opens to a lower exterior 494 of the receiver base 470. The laterally opening slot 490 is also sized and shaped to cooperate with the bottom curved slot 492 to allow for hinged motion of the shank 432 of about thirty degrees on either side of the axis R as partially illustrated in phantom in FIG. 53.

The insert 435 includes a concave upper surface 498A and a convex lower surface 498B and further has a laterally opening U-shaped aperture or slot 499. The insert 436 is sized and shaped to be received in the curved laterally opening slot 190 of the receiver 434 with the aperture 499 receiving the cylindrical surface 448 of the shank 432.

To assemble the bone screw 430, the shank 432 is top- or down-loaded into the receiver 434 tip 444 first into the channel upper opening 477 with the wings 456 of the end portion 438 directed towards the openings of the U-shaped channel 476 as illustrated in FIG. 52. The shank 432 is moved downwardly until the wings 456 abut against the lower seat 478 defining the U-shaped channel 476 of the receiver 434. Then, the insert 435 is slid into the slot 490 until the cylindrical surface 448 is received in and engaged with the insert 436 at the U-shaped aperture 499. As illustrated in FIG. 53, the shank 432 freely moves within the receiver 434 through the axis R and in a plane that includes both the arms 472 and 473. The hinged motion of the shank body 436 is limited by the bottom curved slot 492. When force is placed on the upper shank surface 460, the shank end portion 438 frictionally engages the lower seat 478 of the receiver 434 compressing the lateral slot 490 such that the receiver surfaces defining the slot 490 frictionally engage the insert 435 at the top surface 498A thereof and also at the bottom surface 498B thereof, locking the shank body 436 into an angular position with respect to the receiver 434.

With reference to FIG. 55 an alternative polyaxial bone screw, generally 501 of the invention and an alternative longitudinal connecting member, generally 505, for use in the invention, are illustrated. The polyaxial bone screw 501 includes a shank 508, a receiver 510 and a retaining and articulating structure 512. The shank 508 further includes a threaded shank body 516 and an integral shank upper portion 518. The illustrated receiver 510 includes tool attachment structure generally, 520 for cooperating and engaging with the insertion tool 14 identical to the attachment structure disclosed previously herein with respect to the receiver 26 of the bone screw assembly 1, including, but not limited to the grooves 86 and 87 and cooperating slits 94 and 95, such that the insertion tool 14, the reduction tool 18 and the closure starter 20 may be properly aligned and engaged with the closure structure 28 which in turn engages the receiver 510, with some modification to such tools, if necessary, to allow for cooperation with different types of longitudinal members. Furthermore, a modified driving tool (not shown) for rotating and driving the bone screw 501 into a vertebra, similar to the driving tool 16, includes alignment and centering tabs for engagement with the insertion tool 14, but also includes a driving socket for engagement with the bone screw shank upper portion 518 in lieu of the driving end 234.

The illustrated receiver 510 is further sized and shaped to cooperate and engage with the closure structure 28 previously described herein or other suitable bone screw closure structure. The bone screw 510 is described in greater detail in U.S. Provisional Application 60/728,912 filed Oct. 21, 2005, the disclosure of which is incorporated herein by reference. Another bone screw assembly for use with longitudinal connecting members, insertion tools and reduction tools of the present invention is described in U.S. Provisional Application 60/725,445, filed Oct. 11, 2005, the disclosure of which is also incorporated by reference herein. In the '445 application, the illustrated bone screw assembly further includes upper and lower compression structures sized and shaped to engage an outer coil-like member, but not an inner cylindrical rod core that is free to slide within the coil-like member, the upper and lower compression structures preventing the coil-like member from pressing or crushing against the inner cylindrical core.

The illustrated longitudinal connecting member 505 cooperates with two or more bone screws 501 and is a non-fusion dynamic stabilization longitudinal connecting member assembly having an outer, cannulated coil-like connecting member 530 and one or more threaded inserts 532. The member 505 is described in detail in U.S. Provisional Application 60/728,912, filed Oct. 21, 2005, the disclosure of which is incorporated by reference herein. Furthermore, a dynamic fixation assembly with a coil-like member similar to the member 530 and having a single elongate threaded core is described in U.S. Provisional Application 60/736,112 filed Nov. 10, 2005, the disclosure of which is incorporated by reference herein. Also according to the invention, a solid cylindrical core or insert (not shown) may replace the insert 532 and be attached to the core at only one end thereof and be slidingly receivable within the core along a substantial or entire length of the coil-like member 530. Such an embodiment is illustrated and described in U.S. Provisional Application 60/725,445 filed Oct. 11, 2005, the disclosure of which is incorporated by reference herein. Furthermore, longitudinal connecting members made from solid rods or rods having solid or substantially hollow portions of non-uniform cross-section may be used with bone screw assemblies and tools according to the invention. Examples of such connecting members are described in U.S. Provisional Application 60/722,300 filed Sep. 30, 2005, the disclosure of which is incorporated by reference herein.

It is to be understood that while certain forms of the present invention have been illustrated and described herein, it is not to be limited to the specific forms or arrangement of parts described and shown.

What is claimed and desired to be secured by Letters Patent is as follows:

1. In an insertion tool having an elongated body with a tool attachment structure at a lower end thereof releasably securable to an implant, the insertion tool comprising:
    a) a laterally opening channel formed in the elongated body and communicating with an interior of the body, the lateral opening extending from a top end of the elongated body to the bottom end thereof and providing side access to the interior of the elongated body along the entire length thereof, at least a portion of the opening receiving a longitudinal connecting member; and
    b) a guide and advancement structure disposed on the elongated body interior spaced from the lower end and rotatably mating with a second guide and advancement structure of a reduction tool holding a closure structure, the guide and advancement structure having a starting location selected for synchronized cooperation with an attached implant to precisely mate with the closure structure being rotated and moved into the implant by the reduction tool and place the closure structure at an exact location within the implant.

2. The insertion tool of claim 1 further comprising first and second pins threadably attached to the insertion tool, each pin being elongated and having a bottom surface frictionally engageable with a top surface of an implant being held by the insertion tool, the pins cooperating with the insertion tool and the implant to prohibit slippage between the insertion tool and the implant.

3. The insertion tool of claim 1, wherein the implant has arms, each having an outer surface having an tool engagement structure, the tool engagement structure cooperating with attachment structure on the insertion tool.

4. The insertion tool of claim 3, wherein the implant arms outer surfaces are substantially planar and the tool engagement structure includes an undercut surface.

5. The insertion tool according to claim 1, further comprising:
 a) an engagement portion at the bottom end of the body, including a pair of opposed bone anchor engagement recesses releasably engaging a bone anchor tool engagement structure, each recess including a raised strip releasably mating with a cooperating slit of the bone anchor tool engagement structure.

6. In an insertion tool having an elongated body with attachment structure at a lower end thereof and secured to a spinal implant, the insertion tool comprising:
 a) a traverse through bore defining an interior of the body;
 b) a laterally opening channel formed in the body and communicating with the interior of the body, the lateral opening extending from a bottom end of the body along a substantial length thereof and providing side access to the interior of the body, at least a portion of the opening receiving a longitudinal connecting member; and
 c) a guide and advancement structure disposed on the body interior spaced from the lower end and rotatably mating with a second guide and advancement structure of a reduction tool holding a closure structure, the guide and advancement structure having a starting location selected for synchronized cooperation with an attached spinal implant precisely mating with the closure structure being rotated and moved into the implant by the reduction tool and place the closure structure at an exact location within the implant.

7. The insertion tool of claim 6, further comprising:
 a) including a pair of opposed bone anchor engagement recesses releasably engaging a bone anchor tool engagement structure, each recess including a raised strip releasably mating with a cooperating slit of the bone anchor tool engagement structure.

8. In an insertion tool having an elongated body with an attachment structure at a lower end thereof and secured to an implant receiver, the elongated body preventing splay and rotation with respect to the receiver, the insertion tool comprising:
 a) a laterally opening channel formed in the elongated body and communicating with an interior longitudinal bore of the elongated body, the lateral opening extending upwardly from a lower end of the elongated body, a portion of the opening accommodating a longitudinal connecting member; and
 b) a guide and advancement structure disposed on the elongated body interior and spaced from the lower end thereof, the structure rotating mating with a second guide and advancement structure of a longitudinal connecting member reduction tool.

9. The insertion tool of claim 8, wherein the guide and advancement structure further comprising a starting location selected for synchronized cooperation with an attached implant to precisely mate a closure structure being rotated and moved into the implant by the reduction tool and place the closure structure at an exact location within the implant.

10. In an insertion tool having an elongated body with attachment structure at a lower end thereof and secured to an implant receiver having a horizontal groove near a top surface thereof, and extending from a flat front surface to a flat back surface of the receiver, the insertion tool comprising:
 a) a laterally opening channel formed in the elongated body and communicating with an interior longitudinal bore of the elongated body, the lateral opening extending upwardly from a lower end of the elongated body, a portion of the opening accommodating a longitudinal connecting member; and
 b) a guide and advancement structure disposed on the body interior and spaced from the lower end thereof, the structure rotating mating with a second guide and advancement structure of a longitudinal connecting member reduction tool.

11. The insertion tool of claim 10, wherein the guide and advancement structure further comprising a starting location selected for synchronized cooperation with an attached implant to precisely mate a closure structure being rotated and moved into the implant by the reduction tool and place the closure structure at an exact location within the implant.

12. In an insertion tool having an elongated body with attachment structure at a lower end thereof and secured to an implant receiver having a horizontal groove near a top surface thereof, and extending from a flat front surface to a flat back surface of the receiver, the insertion tool comprising:
 a) a laterally opening channel formed in the elongated body and communicating with an interior longitudinal bore of the body, the bore extending an entire length of the body, the lateral opening extending upwardly from a lower end of the elongated body along a length thereof, a portion of the opening accommodating a longitudinal connecting member; and
 b) a guide and advancement structure disposed on a portion of the elongated body interior bore and spaced from the lower end thereof, the structure rotating mating with a second guide and advancement structure of a longitudinal connecting member reduction tool.

13. A insertion tool comprising:
 a) an elongated body with a tool attachment structure at a lower end thereof, the tool attachment structure releasably secured to an implant, the implant having a receiver with a first channel formed by a pair of upwardly extending arms with internal surfaces having threads, each arm external surface having structure attachable to the tool attachment structure;
 b) a through bore defining an interior of the elongated body of the tool, the interior having tool threads formed in the elongated body of the tool at an upper portion thereof opposite the lower end of the elongated body, the tool threads rotatable mating with a guide and advancement structure of a reduction tool, the reduction tool reducing a longitudinal connecting member down into the first channel of the receiver releasably secured to the tool; and
 c) a laterally opening channel formed in the elongated body and communicating with the interior of the elongated body, the laterally opening second channel extending upwardly from the lower end of the elongated body toward the upper portion thereof providing side access to the interior of the elongated body, a portion of the laterally opening second channel receiving the longitudinal connect member.

* * * * *